(12) United States Patent
Yassinzadeh et al.

(10) Patent No.: US 10,327,747 B2
(45) Date of Patent: *Jun. 25, 2019

(54) APPARATUS AND METHODS FOR DELIVERING HEMOSTATIC MATERIALS FOR BLOOD VESSEL CLOSURE

(71) Applicant: Cardiva Medical, Inc., Santa Clara, CA (US)

(72) Inventors: Zia Yassinzadeh, San Jose, CA (US); Delfin Pelayo, San Jose, CA (US)

(73) Assignee: Cardiva Medical, Inc., Santa Clara, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/237,493

(22) Filed: Aug. 15, 2016

(65) Prior Publication Data

US 2016/0345946 A1    Dec. 1, 2016

Related U.S. Application Data

(63) Continuation of application No. 14/542,066, filed on Nov. 14, 2014, now Pat. No. 9,439,637, which is a
(Continued)

(51) Int. Cl.
*A61B 17/00* (2006.01)
*A61B 90/00* (2016.01)
*A61B 17/22* (2006.01)

(52) U.S. Cl.
CPC .......... *A61B 17/0057* (2013.01); *A61B 90/39* (2016.02); *A61B 2017/00004* (2013.01);
(Continued)

(58) Field of Classification Search
CPC ...... A61B 17/0057; A61B 2017/00637; A61B 2017/00004; A61B 2017/00659
(Continued)

(56) References Cited

U.S. PATENT DOCUMENTS 4,650,466 A    3/1987    Luther
4,723,549 A    2/1988    Wholey et al.
(Continued)

FOREIGN PATENT DOCUMENTS

WO    WO-9222252 A1    12/1992
WO    WO-9505121 A1    2/1995
(Continued)

OTHER PUBLICATIONS

European search report and search opinion dated Mar. 7, 2014 for EP Application No. 9774368.6.
(Continued)

*Primary Examiner* — Katherine M Shi
(74) *Attorney, Agent, or Firm* — Wilson Sonsini Goodrich and Rosati, P.C.

(57) ABSTRACT

Apparatus for sealing a vascular wall penetration disposed at the end of the tissue tract comprises a shaft, an occlusion element, a hemostatic implant, and a protective sleeve. The apparatus is deployed through the tissue tract with the occlusion element temporarily occluding the vascular wall penetration and inhibiting backbleeding therethrough. The hemostatic implant, which will typically be a biodegradable polymer such as collagen carrying an anti-proliferative agent or coagulation promoter, will then be deployed from the sealing apparatus and left in place to enhance closure of the vascular wall penetration with minimum scarring. The implant may be radiopaque to allow observation before release.

19 Claims, 17 Drawing Sheets

Related U.S. Application Data continuation of application No. 13/452,656, filed on Apr. 20, 2012, now Pat. No. 8,911,472, which is a continuation-in-part of application No. 12/492,779, filed on Jun. 26, 2009, now abandoned.

(60) Provisional application No. 61/077,104, filed on Jun. 30, 2008.

(52) U.S. Cl.
CPC ........... *A61B 2017/00623* (2013.01); *A61B 2017/00654* (2013.01); *A61B 2017/00893* (2013.01); *A61B 2017/00898* (2013.01); *A61B 2017/22067* (2013.01); *A61B 2090/3966* (2016.02)

(58) Field of Classification Search
USPC ....................................................... 606/213
See application file for complete search history.

(56) References Cited

U.S. PATENT DOCUMENTS

| | | |
|---|---|---|
| 4,744,364 A | 5/1988 | Kensey |
| 4,852,568 A | 8/1989 | Kensey |
| 4,890,612 A | 1/1990 | Kensey |
| 4,895,168 A | 1/1990 | Machek |
| 4,921,484 A | 5/1990 | Hillstead |
| 5,041,093 A | 8/1991 | Chu |
| 5,061,271 A | 10/1991 | Van Zile |
| 5,061,274 A | 10/1991 | Kensey |
| 5,108,420 A | 4/1992 | Marks |
| 5,108,421 A | 4/1992 | Fowler |
| 5,171,259 A | 12/1992 | Inoue |
| 5,197,971 A | 3/1993 | Bonutti |
| 5,222,974 A | 6/1993 | Kensey et al. |
| 5,258,000 A | 11/1993 | Gianturco |
| 5,263,963 A | 11/1993 | Garrison et al. |
| 5,290,552 A | 3/1994 | Sierra et al. |
| 5,292,332 A | 3/1994 | Lee |
| 5,370,660 A | 12/1994 | Weinstein et al. |
| 5,383,896 A | 1/1995 | Gershony et al. |
| 5,419,765 A | 5/1995 | Weldon et al. |
| 5,454,833 A | 10/1995 | Boussignac et al. |
| 5,456,667 A | 10/1995 | Ham et al. |
| 5,486,195 A | 1/1996 | Myers et al. |
| 5,507,744 A | 4/1996 | Tay et al. |
| 5,527,282 A | 6/1996 | Segal |
| 5,540,715 A | 7/1996 | Katsaros et al. |
| 5,626,601 A | 5/1997 | Gershony et al. |
| 5,630,833 A | 5/1997 | Katsaros et al. |
| 5,634,936 A | 6/1997 | Linden et al. |
| 5,649,959 A | 7/1997 | Hannam et al. |
| 5,653,730 A | 8/1997 | Hammerslag |
| 5,725,551 A | 3/1998 | Myers et al. |
| 5,728,133 A | 3/1998 | Kontos |
| 5,728,134 A | 3/1998 | Barak |
| 5,749,883 A | 5/1998 | Halpern |
| 5,782,860 A | 7/1998 | Epstein et al. |
| 5,810,810 A | 9/1998 | Tay et al. |
| 5,810,866 A | 9/1998 | Yoon |
| 5,836,913 A | 11/1998 | Orth et al. |
| 5,851,210 A | 12/1998 | Torossian |
| 5,861,003 A | 1/1999 | Latson et al. |
| 5,868,778 A | 2/1999 | Gershony et al. |
| 5,895,398 A | 4/1999 | Wensel et al. |
| 5,922,009 A | 7/1999 | Epstein et al. |
| 5,951,583 A | 9/1999 | Jensen et al. |
| 5,951,589 A | 9/1999 | Epstein et al. |
| 5,957,952 A | 9/1999 | Gershony et al. |
| 6,007,563 A | 12/1999 | Nash et al. |
| 6,012,457 A | 1/2000 | Lesh |
| 6,017,359 A | 1/2000 | Gershony et al. |
| 6,022,361 A | 2/2000 | Epstein et al. |
| 6,045,569 A | 4/2000 | Kensey et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,071,300 A | 6/2000 | Brenneman et al. |
| 6,080,182 A | 6/2000 | Shaw et al. |
| 6,126,675 A | 10/2000 | Shchervinsky et al. |
| 6,146,396 A | 11/2000 | Konya et al. |
| 6,162,240 A | 12/2000 | Cates et al. |
| 6,193,670 B1 | 2/2001 | Van Tassel et al. |
| 6,248,124 B1 | 6/2001 | Pedros et al. |
| 6,296,657 B1 | 10/2001 | Brucker |
| 6,464,712 B1 | 10/2002 | Epstein et al. |
| 6,547,803 B2 | 4/2003 | Seward et al. |
| 6,554,851 B1 | 4/2003 | Palasis et al. |
| 6,569,185 B2 | 5/2003 | Ungs |
| 6,610,026 B2 | 8/2003 | Cragg et al. |
| 6,656,207 B2 | 12/2003 | Epstein et al. |
| 6,743,195 B2 | 6/2004 | Zucker |
| 6,913,614 B2 | 7/2005 | Marino et al. |
| 6,939,363 B2 | 9/2005 | Akerfeldt et al. |
| 6,984,219 B2 | 1/2006 | Ashby et al. |
| 6,989,022 B2 | 1/2006 | Nowakowski |
| 7,008,439 B1 | 3/2006 | Janzen et al. |
| 7,008,441 B2 | 3/2006 | Zucker |
| 7,025,776 B1 | 4/2006 | Houser et al. |
| 7,115,127 B2 | 10/2006 | Lindenbaum et al. |
| 7,223,266 B2 | 5/2007 | Lindenbaum et al. |
| 7,232,454 B2 | 6/2007 | Rousseau |
| 7,335,219 B1 | 2/2008 | Ashby et al. |
| 7,335,220 B2 | 2/2008 | Khosravi et al. |
| 7,361,183 B2 | 4/2008 | Ginn |
| 8,911,472 B2 | 12/2014 | Yassinzadeh et al. |
| 2002/0072767 A1 | 6/2002 | Zhu et al. |
| 2002/0072768 A1 | 6/2002 | Ginn |
| 2002/0133123 A1 | 9/2002 | Zucker |
| 2003/0018357 A1 | 1/2003 | Luthra et al. |
| 2003/0045835 A1 | 3/2003 | Anderson et al. |
| 2003/0055454 A1 | 3/2003 | Zucker |
| 2003/0100921 A1 | 5/2003 | Addis et al. |
| 2003/0125766 A1 | 7/2003 | Ding |
| 2003/0163146 A1 | 8/2003 | Epstein et al. |
| 2003/0191493 A1 | 10/2003 | Epstein et al. |
| 2004/0172060 A1 | 9/2004 | Cates et al. |
| 2004/0176758 A1 | 9/2004 | Yassinzadeh |
| 2004/0176798 A1 | 9/2004 | Epstein et al. |
| 2004/0243052 A1 | 12/2004 | Kauphusman et al. |
| 2004/0267308 A1 | 12/2004 | Bagaoisan et al. |
| 2005/0004158 A1 | 1/2005 | Iyer et al. |
| 2005/0038472 A1 | 2/2005 | Furst |
| 2005/0065549 A1 | 3/2005 | Cates et al. |
| 2005/0216054 A1 | 9/2005 | Widomski et al. |
| 2005/0228443 A1 | 10/2005 | Yassinzadeh |
| 2005/0228444 A1 | 10/2005 | Wendlandt |
| 2005/0267522 A1 | 12/2005 | Yassinzadeh et al. |
| 2005/0277980 A1 | 12/2005 | Yassinzadeh |
| 2006/0034935 A1 | 2/2006 | Pronovost et al. |
| 2006/0088570 A1 | 4/2006 | Cruise et al. |
| 2006/0099238 A1 | 5/2006 | Khosravi et al. |
| 2006/0100664 A1 | 5/2006 | Pai et al. |
| 2006/0106362 A1 | 5/2006 | Pass et al. |
| 2006/0184226 A1 | 8/2006 | Austin |
| 2006/0229670 A1 | 10/2006 | Bates |
| 2007/0032804 A1 | 2/2007 | Modesitt et al. |
| 2007/0038244 A1 | 2/2007 | Morris et al. |
| 2007/0060895 A1 | 3/2007 | Sibbitt et al. |
| 2007/0123817 A1 | 5/2007 | Khosravi et al. |
| 2007/0135837 A1 | 6/2007 | Yassinzadeh |
| 2007/0196421 A1 | 8/2007 | Hunter et al. |
| 2007/0198059 A1 | 8/2007 | Patel et al. |
| 2007/0212388 A1 | 9/2007 | Patravale et al. |
| 2007/0231366 A1 | 10/2007 | Sawhney et al. |
| 2007/0276435 A1 | 11/2007 | Yassinzadeh et al. |
| 2007/0282247 A1 | 12/2007 | Desai et al. |
| 2007/0299043 A1 | 12/2007 | Hunter et al. |
| 2008/0039362 A1 | 2/2008 | Shebuski et al. |
| 2008/0071310 A1 | 3/2008 | Hoffman et al. |
| 2008/0082122 A1 | 4/2008 | Khosravi et al. |

(56) References Cited

U.S. PATENT DOCUMENTS

| | | |
|---|---|---|
| 2008/0154303 A1 | 6/2008 | Yassinzadeh |
| 2010/0168767 A1 | 7/2010 | Yassinzadeh et al. |
| 2012/0209321 A1 | 8/2012 | Yassinzadeh et al. |

FOREIGN PATENT DOCUMENTS

| | | |
|---|---|---|
| WO | WO-9624290 A1 | 8/1996 |
| WO | WO-9624291 A1 | 8/1996 |
| WO | WO-9834546 A1 | 8/1998 |
| WO | WO-9840017 A2 | 9/1998 |
| WO | WO-9840017 A3 | 10/1998 |
| WO | WO-0006029 A1 | 2/2000 |
| WO | WO-0006031 A1 | 2/2000 |
| WO | WO-2006115904 A2 | 11/2006 |

OTHER PUBLICATIONS

International search report and written opinion dated Aug. 31, 2009 for PCT/US2009/049297.
Notice of allowance dated Jun. 16, 2016 for U.S. Appl. No. 14/542,066.
Notice of allowance dated Aug. 15, 2014 for U.S. Appl. No. 13/452,656.
Office action dated Jan. 9, 2012 for U.S. Appl. No. 12/492,779.
Office action dated Mar. 21, 2016 for U.S. Appl. No. 14/542,066.
Office action dated Mar. 27, 2014 for U.S. Appl. No. 13/452,656.
Office action dated Jul. 24, 2012 for U.S. Appl. No. 13/452,656.
Office action dated Sep. 19, 2011 for U.S. Appl. No. 12/492,779.
Office action dated Nov. 21, 2013 for U.S. Appl. No. 13/452,656.
Office action dated Nov. 30, 2015 for U.S. Appl. No. 14/542,066.
Office action dated Dec. 6, 2012 for U.S. Appl. No. 13/452,656.

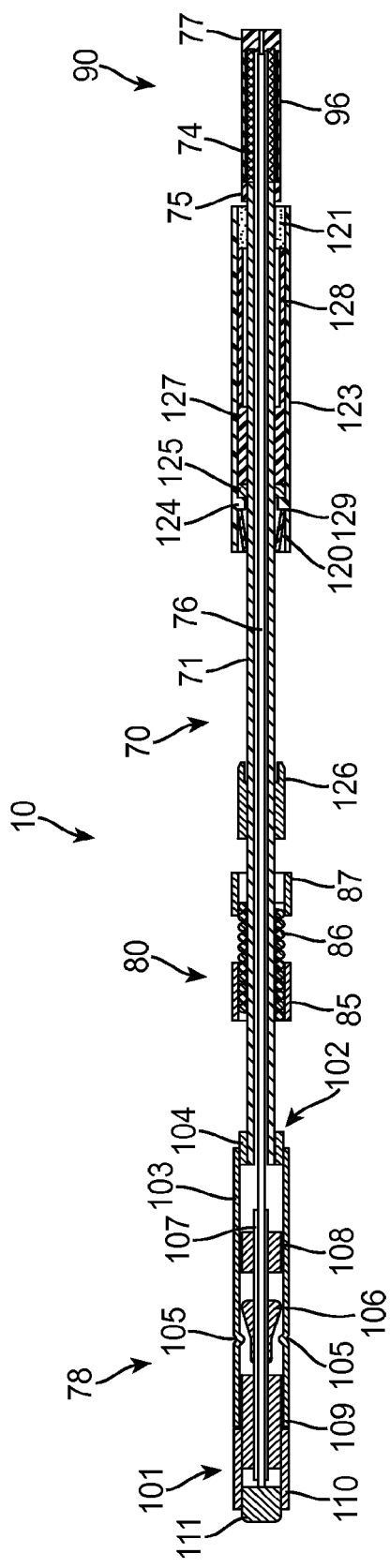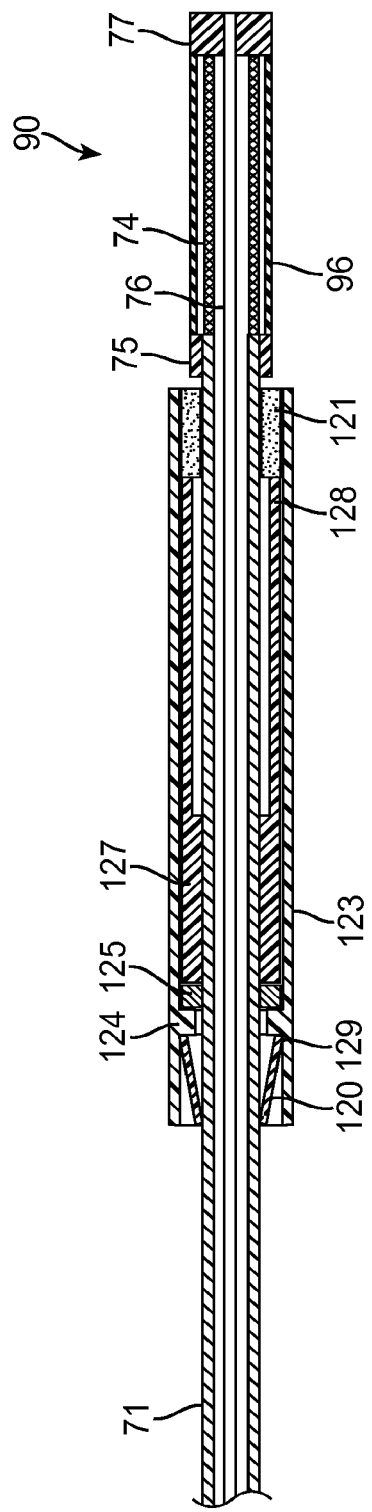
FIG. 1
FIG. 1A

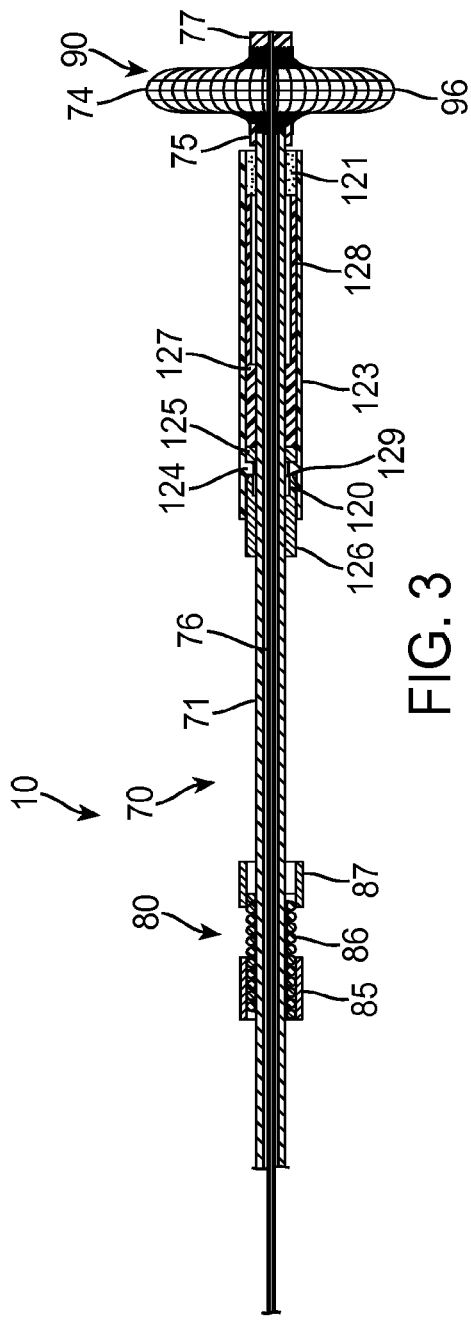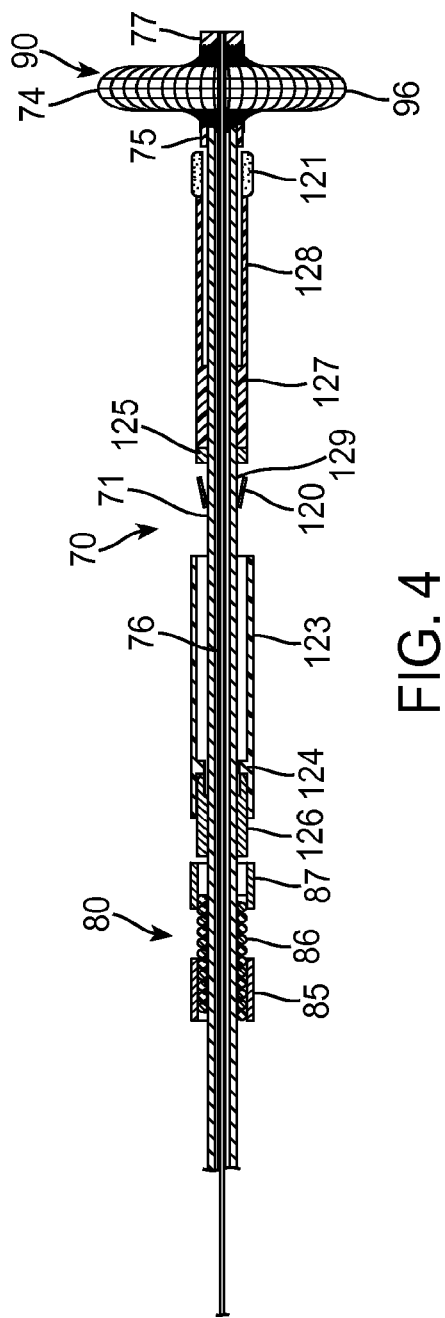

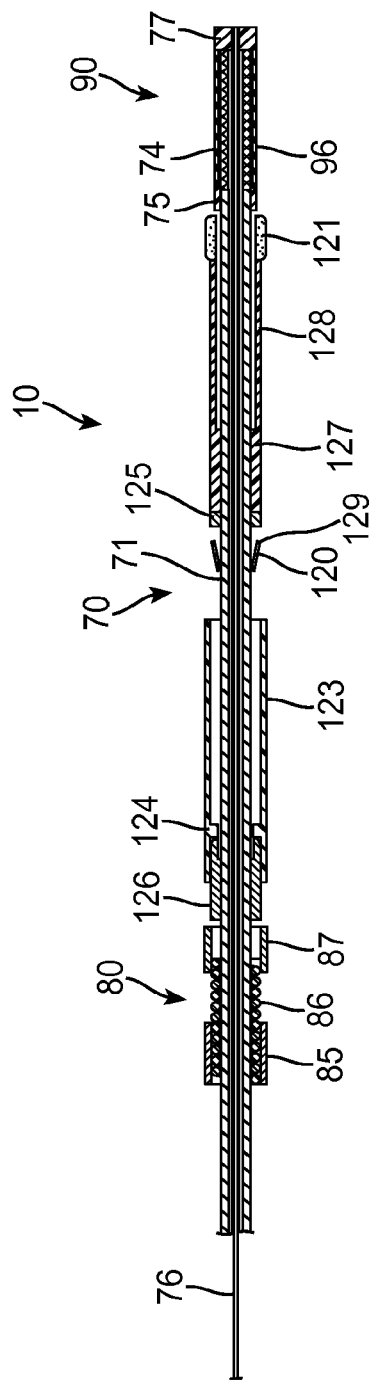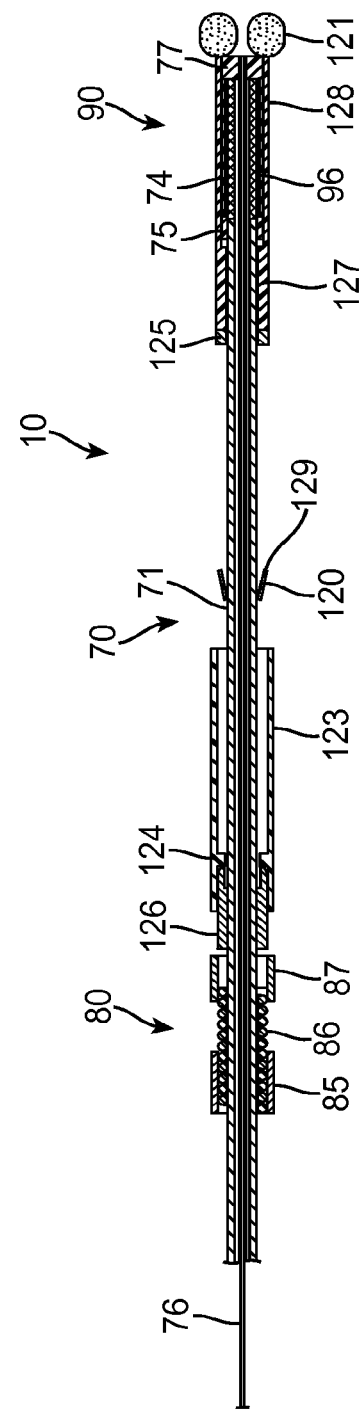

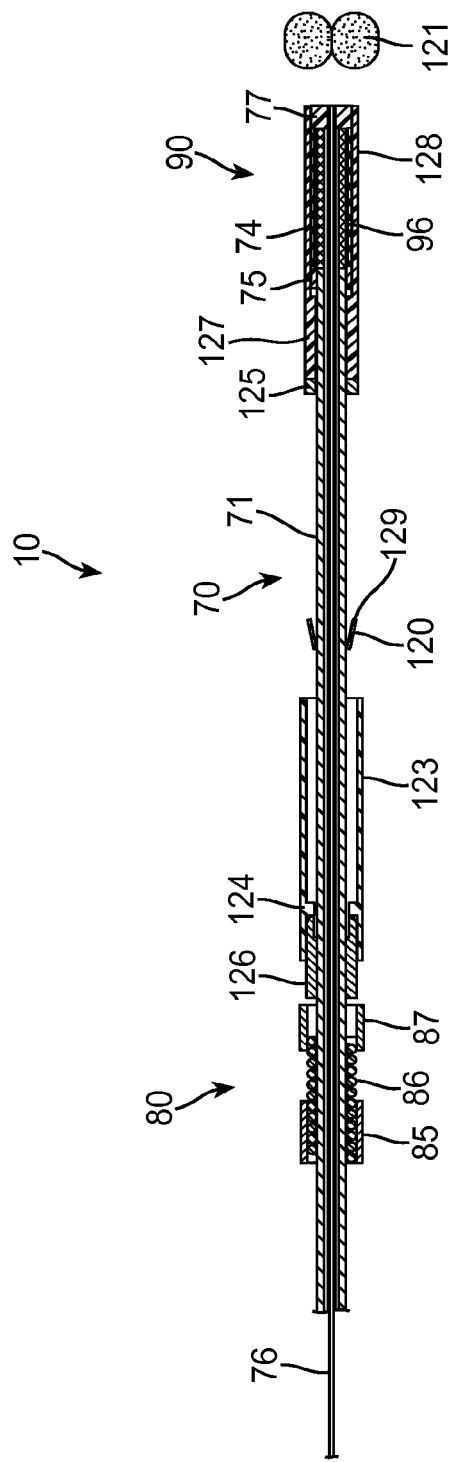

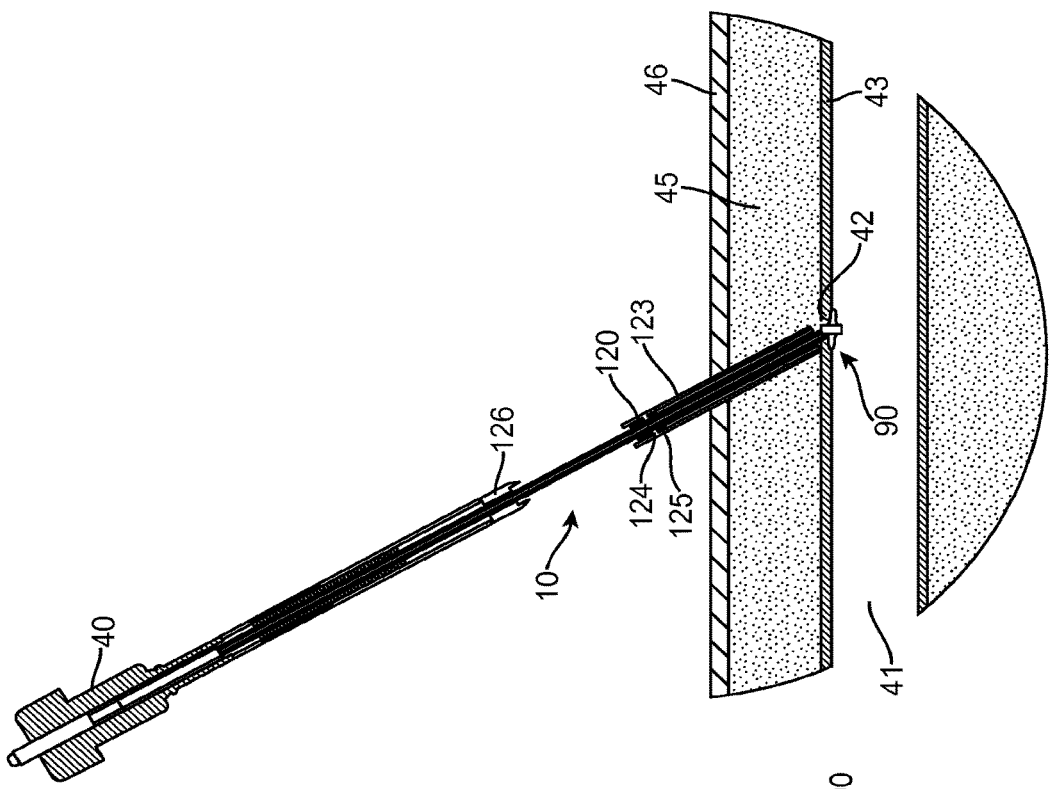
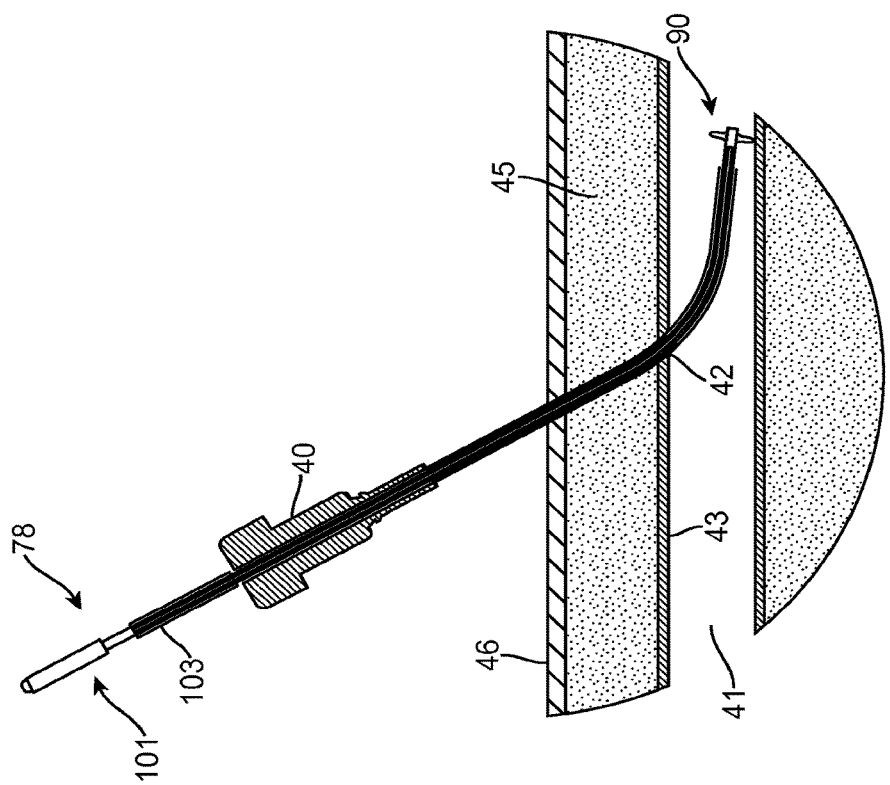

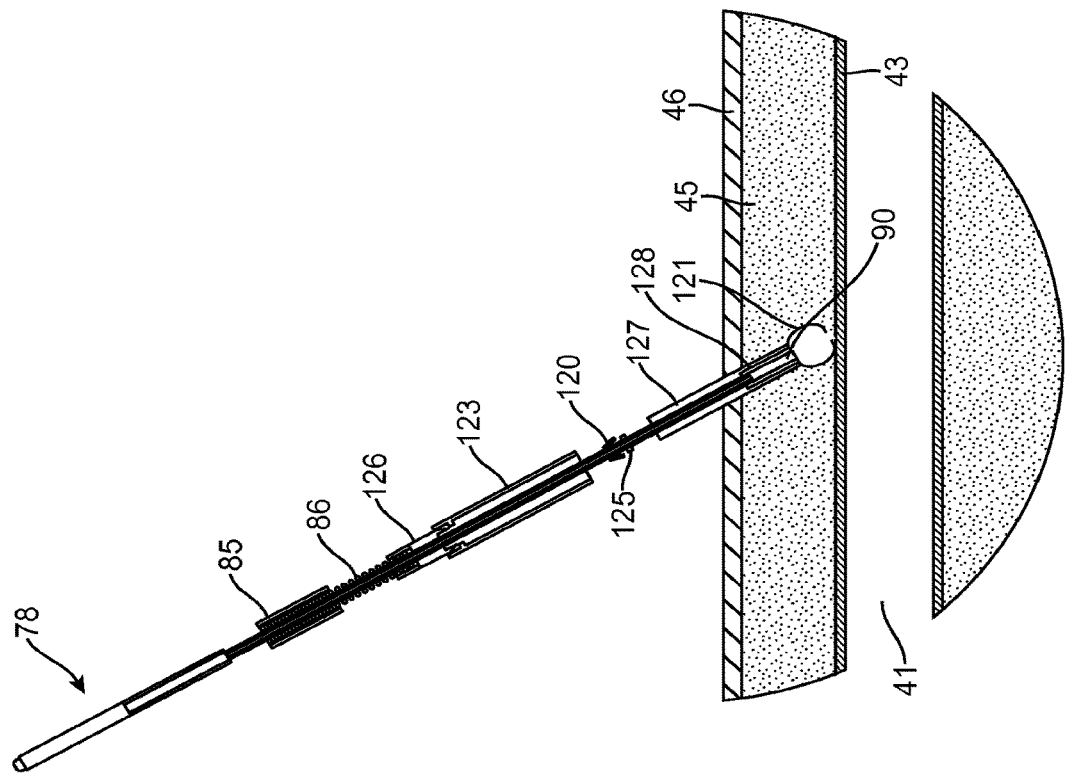
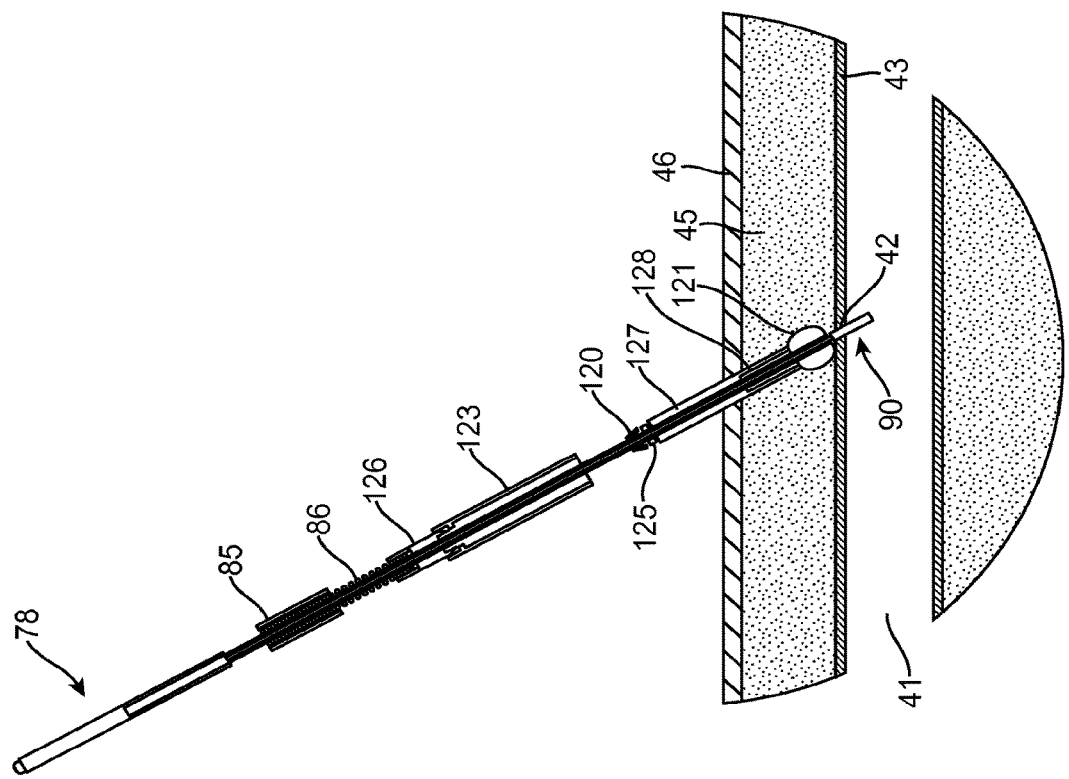

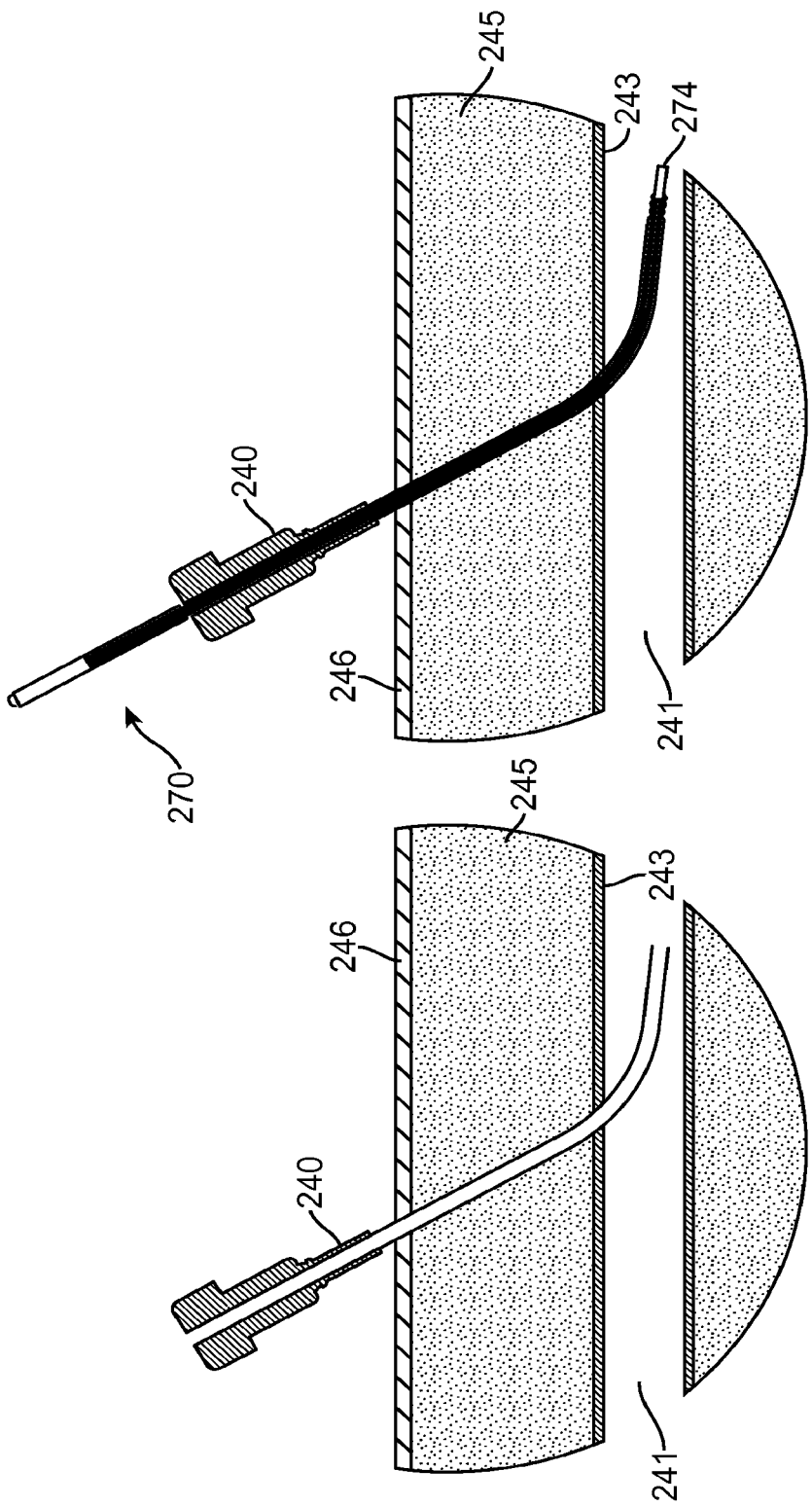

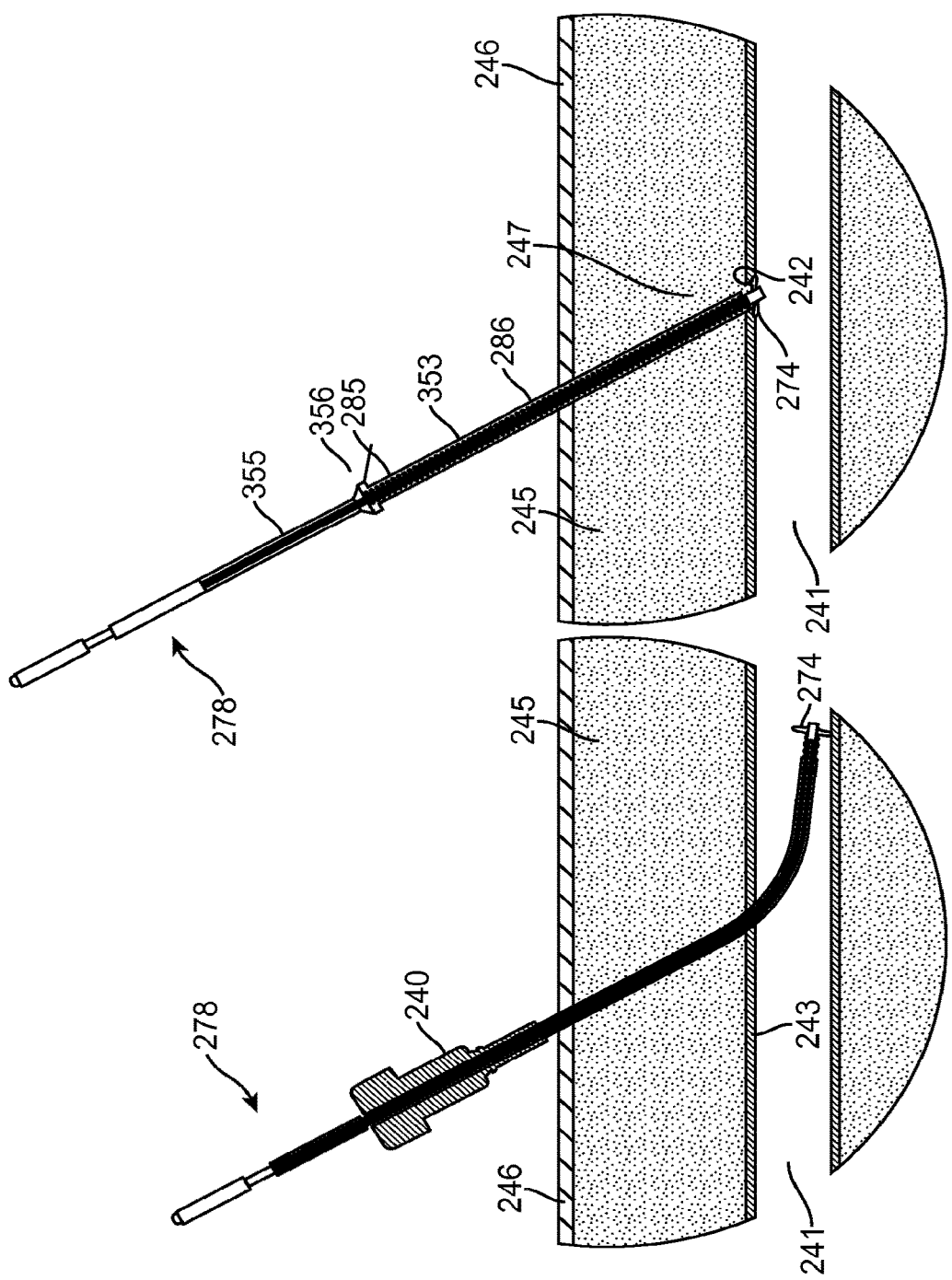

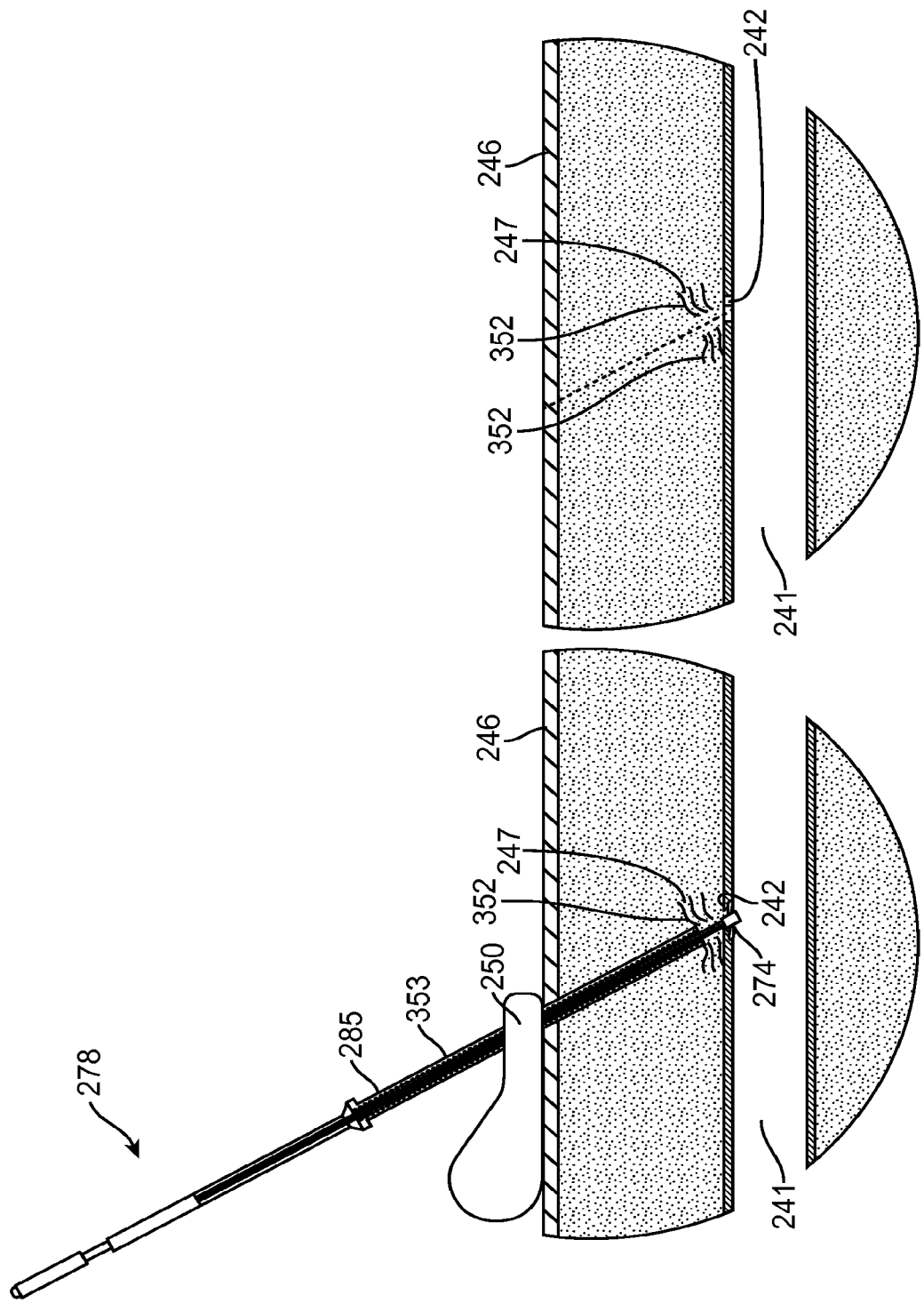

APPARATUS AND METHODS FOR DELIVERING HEMOSTATIC MATERIALS FOR BLOOD VESSEL CLOSURE

CROSS-REFERENCES TO RELATED APPLICATIONS

This application is a continuation of U.S. patent application Ser. No. 14/542,066, filed Nov. 14, 2014, now U.S. Pat. No. 9,439,637, issued on Sep. 13, 2016, which is a continuation of U.S. patent application Ser. No. 13/452,656, filed Apr. 20, 2012, now U.S. Pat. No. 8,911,472, issued on Dec. 16, 2014, which is a continuation-in-part of application Ser. No. 12/492,779, filed on Jun. 26, 2009, which claims the benefit of provisional Application No. 61/077,104, filed on Jun. 30, 2008, the full disclosures of which are incorporated herein by reference.

BACKGROUND OF THE INVENTION

1. Field of the Invention.

The present invention relates generally to medical devices and methods. More particularly, the present invention relates to apparatus and protocols for closing arteriotomies and other vascular wall penetrations.

Angiography, angioplasty, atherectomy, and a number of other vascular and cardiovascular procedures are performed intravascularly and require percutaneous access into the patient's vasculature, most often into the arterial vasculature. The most common technique for achieving percutaneous access is called the Seldinger technique, where access to an artery, typically the femoral artery in the groin, is first established using a needle to form a "tract," i.e., a passage through the tissue overlying the blood vessel. The needle tract is then dilated, and an access sheath is placed into the dilated tract and through a penetration in the vascular wall, such as an arteriotomy to allow the introduction of guidewires, interventional catheters, catheter exchange, and the like to perform the desired procedure.

Once the desired procedure is completed, the access sheath must be removed and the arteriotomy or other vascular wall penetration closed. For many years, such closure was achieved by applying manual pressure onto the patient's skin over the site of the vascular wall penetration. Patients, however, have often been heparinized to limit the risk of thrombosis during the procedure, and clotting of the vascular wall penetration can often take an extended period, particularly when the penetration is relatively large for performing procedures needing larger diameter catheters. For these reasons, improved methods for closing and sealing vascular wall penetrations have been sought.

In the last decade, a variety of new procedures and devices have been introduced to more effectively seal the arteriotomies and other vascular wall penetrations associated with percutaneous intravascular access. Some of the new protocols rely on suturing, others rely on clipping, plug placement, energy-based closure, and the like. One problem with many of the new procedures, however, is that they leave material behind, and/or induce scar formation at the access site. Both the leaving of materials and the formation of scar tissue can be problematic, particularly if the patient requires subsequent access to the same vascular site for performance of another vascular or cardiovascular procedure.

For these reasons, it would be advantageous to provide protocols and apparatus which would leave no material behind and which would further limit the likelihood of forming scar tissue after the procedure is complete. One device that can meet these objectives in many instances is the Boomerang Catalyst™ system available from Cardiva Medical, Inc., assignee of the present application. The Boomerang Catalyst system includes an expansible element at its tip for providing temporary hemostasis when placed in the blood vessel adjacent to the vascular wall penetration. The catheter further includes a catalytic material on its shaft which helps induce hemostasis and clotting within the tissue tract immediately above the vessel wall penetration. The construction and use of this system is described in copending application Ser. Nos. 11/302,951; 11/772,718; and 11/614,276, the full disclosures of which are incorporated herein by reference.

Despite the success of the Boomerang Catalyst systems, there may still be some instances where hemostasis is not achieved as rapidly. For this reason, it would be desirable to provide further improved systems and protocols for closing and sealing arteriotomies and other vascular wall penetrations, where the closure may be achieved with rapid hemostasis, with a minimum risk of scar formation, and without leaving any materials or implants permanently behind in the vessel or the tissue tract. At least some of these objectives will be met by the inventions described below.

2. Background of the Invention.

U.S. Pat. No. 7,335,219 describes a device for delivering a plug of hemostatic material to a location just above a blood vessel wall penetration. The hemostatic material is encapsulated in a dissolvable structure and a non-expandable control tip assembly helps advance the device through the tissue tract and may also provide hemostasis and bleedback. US2007/0123817 and U.S. Pat. No. 7,008,439 describe apparatus for sealing a vascular wall penetration. Other apparatus for closing blood vessel wall punctures are described in U.S. Pat. Nos. 4,744,364; 5,061,271; 5,728,133; and 7,361,183 and U.S. Published Patent Application Nos. 2003/0125766; 2004/0267308; 2006/0088570; 2007/0196421; and 2007/0299043. The incorporation of anti-proliferative materials in hemostatic materials for blood vessel closure and other purposes is described in U.S. Pat. Nos. 7,025,776 and 7,232,454; 6,554,851; and U.S. Published Patent Application Nos. 2005/0004158; 2005/0038472; 2007/0060895/2007/0032804; and 2008/0039362.

BRIEF SUMMARY OF THE INVENTION

The present invention provides apparatus and methods for sealing a blood vessel wall penetration with little or no material being permanently left behind and with a reduced likelihood of scar tissue formation. The invention relies on placing a hemostatic implant in the tissue tract at a location over the vascular wall penetration while the penetration is temporarily closed with an expansible occlusion element present in the blood vessel lumen. The hemostatic implant is preferably biodegradable, typically over a period of less than one year, preferably over a period of less than six months, more preferably less than three months, and may carry an anti-proliferative agent to reduce scar formation. Additionally or alternatively, the implant may carry a coagulation promoter to accelerate hemostasis and/or radiopaque material to enhance visualization. The use of the hemostatic implant together with the temporary hemostasis provided by the occlusion element increases the likelihood that even relatively large vascular penetrations can be successfully closed and usually reduces the time needed to achieve such closure.

Apparatus according to the present invention for sealing a blood vessel wall penetration disposed at an end of a tissue tract comprise a shaft, an occlusion element, a hemostatic implant, and a protective sleeve. The shaft has a proximal and distal end and is adapted to be introduced through the tissue tract so that the shaft distal end can be positioned within the blood vessel lumen. Usually, the shaft will be adapted so that it can be introduced through the vascular access sheath which is in place after performance of the interventional procedure.

The occlusion element is disposed near the distal end of the shaft and is configured so that it may be shifted between a radially contracted configuration which facilitates introduction through the tissue tract and a radially expanded configuration for deployment within the blood vessel to occlude the penetration and provide temporary hemostasis. The hemostatic element could be a balloon or other inflatable structure, but will more usually be an expansible braid, coil, or other element which may be radially expanded by axial foreshortening. Typically, the shaft comprises an outer tube and an inner rod where a distal end of the occlusion element is attached to a distal end of the rod and a proximal end of the occlusion element is attached to a distal end of the outer tube. Thus, the occlusion element can be expanded and contracted by retracting and advancing the rod relative to the tube, respectively. The preferred occlusion element comprises a braided mesh covered with an elastic membrane. As described thus far, the shaft and occlusion element may be similar or identical to those described in the earlier referenced commonly owned patent applications.

The hemostatic implant of the present invention is disposed over an exterior surface of the shaft proximal to the occlusion element. The protective sleeve is retractably disposed over the hemostatic implant to protect it while the shaft is being introduced to the tissue tract. The hemostatic implant will typically comprise a body or wrapped sheet which partially or fully circumscribes the shaft, but other configurations could also be utilized. In a first embodiment, the hemostatic implant comprises a cylindrical body which is coaxially mounted about the shaft of the delivery device. Such fully circumscribing implants, however, can have difficulty being released from the shaft after they are exposed and hydrated. Thus, it will often be preferable to provide hemostatic implant configurations where the body partially circumscribes the shaft or is disposed in parallel to the shaft. When the implant is not disposed about the shaft, release upon rehydration will be greatly simplified as the rehydrated implant will lie adjacent to the shaft, allowing the shaft and the collapsed occlusion element to be drawn proximally past the rehydrated hemostatic implant with minimum interference. The hemostatic implant typically comprises a swellable, biodegradable polymer which swells upon hydration. Hydration is prevented when the polymer is introduced by the protective sleeve. The polymer hydrates and swells when the sleeve is retracted within the tissue tract, exposing the polymer to the body fluids. Suitable polymers include biodegradable hydrogels such as polyethylene glycols, collagens, gelatins, and the like.

An anti-proliferative agent will usually be distributed within or otherwise carried by the material of the hemostatic implant. As most anti-proliferative agents, such as sirolimus, paclitaxel, and the like, are hydrophobic, it will usually be desirable to incorporate the anti-proliferative agents in a carrier, such as a biodegradable polymer, such a polylactic acid (PLA), poly(lactide-co-glycolide), and the like. The anti-proliferative agents may be incorporated into pores of polymeric beads or other structures which are dispersed or distributed within the biodegradable hydrogel or other swellable polymer. In certain embodiments, the anti-proliferative agents may be incorporated into nanoparticles, typically having dimensions in the range from 10 nm to 100 .mu.m.

Agents useful as coagulation promoters, such as thrombin, tissue factors, components of the clotting cascade, and the like may also be incorporated into the body of the hemostatic implant. In some instances, it may be desirable to incorporate such coagulation promoters into particulate or other carriers as described above with regard to the anti-proliferative agents.

In addition to the anti-proliferative agents and the coagulation promoters, the hemostatic implants of the present invention may further incorporate radiopaque materials in or on at least a portion of the implant body. For example, a radiopaque material, such as barium, may be incorporated into the polymer, either by dispersion or chemical bonding. Alternatively, radiopaque rings, markers, and other elements, may be attached on or to the hemostatic implant, for example at each end of the implant to facilitate visualization of the implant as it is being implanted. Additionally or alternatively, radiopaque markers may be provided on the tube or shaft which carries the hemostatic implant so that the marker(s) align with a portion of the implant, typically either or both ends of the implant, prior to deployment.

In a preferred aspect of the present invention, the protective sleeve is held in place by a latch mechanism while it is being introduced. A separate key element is provided to release the latch mechanism and permit retraction of the sleeve after the device has been properly placed through the tissue tract and into the target blood vessel. The latch will be disposed on the shaft and will engage the protective sleeve to immobilize the sleeve during introduction. The key, which is usually slidably disposed on the shaft proximal of the latch, is able to shift the latch between a locking configuration where the sleeve is immobilized and an open configuration which allows the sleeve to be proximally retracted. Usually, the latch is spring-loaded to deflect radially outwardly from the shaft in a manner which engages the sleeve. The key is then adapted to radially depress the latch to release the sleeve. In a preferred embodiment, the latch and key mechanism will extend over a proximal portion of the shaft having a length sufficient to allow manual access to the key latch even when the shaft is placed in the tissue tract.

In a further preferred aspect of the present invention, a backstop structure is provided on the shaft to engage the hemostatic implant to immobilize the implant while the sleeve is being proximally refracted. The backstop usually comprises a tube disposed on or coaxially over the shaft and having a distal end which engages a proximal end of the hemostatic implant. The backstop engages the hemostatic implant to prevent accidental dislodgement while the occlusion element is being proximally retracted through the implant. The backstop may include a space or receptacle for receiving the retracted occlusion element, allowing the backstop to be held in place until the occlusion element has been fully retracted through the hemostatic implant.

The protective sleeve of the present invention may comprise an outer sleeve and a separately retractable inner release sheath. The outer sleeve and inner release sheath are usually mounted coaxially so that the outer sleeve may be retracted over the inner release sheath while the inner release sheath remains stationary over the implant and acts as a friction barrier between the outer sleeve and implant. Without the inner release sheath, the protective sleeve, which applies the compressive and constrictive forces to the hemostatic implant, could stick to the hemostatic implant and make retraction of the protective sleeve and deployment of the implant difficult. The inner release sheath is preferably axially split so that, once the outer sleeve is retracted, the inner release sheath opens to release the implant and facilitate retraction of the release sheath. In preferred embodiments, the outer sleeve can engage the inner release sheath after the outer sleeve has been partly retracted. During the remainder of the outer sleeve retraction, the outer sleeve will then couple to and retract the inner release sheath to fully release the hemostatic implant. In addition to the use of the inner release sheath, the distal end of the protective sleeve may be sealed with a biodegradable substance, such as a glycerin gel, which can inhibit premature hydration of the hemostatic implant prior to release.

In a further preferred aspect of the present invention, the key of the latch mechanism can include a coupling element which attaches to the protective sleeve as the key is advanced and the latch is released. After the key couples to the protective sleeve, the key can be used to retract the protective sleeve. That is, rather than having to reposition the hand to grab and retract the protective sleeve which would also retract the mating key, only the key needs to be held and retracted.

Methods according to the present invention for sealing a blood vessel penetration disposed at the end of a tissue tract comprise providing an apparatus including a shaft, an occlusion element, and a hemostatic implant disposed on an exterior surface of the shaft. The shaft is introduced through the tissue tract to position the occlusion element in the lumen of the blood vessel and the hemostatic implant within the tissue tract. The hemostatic implant is covered by a protective sleeve while the shaft is being introduced through the tissue tract, and the occlusion element is deployed to temporarily inhibit blood flow from the blood vessel into the tissue tract. The protective sleeve is then retracted to expose the hemostatic implant, where the implant typically absorbs fluid and expands to provide the desired seal within the tissue tract. After the hemostatic implant has expanded sufficiently, the occlusion element will be collapsed, and the shaft and collapsed occlusion element withdrawn leaving the hemostatic implant in the tissue tract. As described above, it will usually be preferred to position the hemostatic implant laterally or to the side of the shaft which carries the occlusion element. By thus positioning the occlusion element to bypass the hydrated hemostatic implant, withdrawal of the collapsed occlusion element past the hydrated hemostatic implant can be greatly facilitated. Preferably, the material of the hemostatic implant will degrade over time, preferably over a period of less than one year, more preferably over a period of less than six months, usually less than three months, leaving no material behind at the vascular access point.

In a preferred aspect of the methods of the present invention, the protective sleeve is latched to the shaft while the shaft is introduced. By "latched" is meant that the sleeve will be fixed or immobilized to the shaft by some mechanical link, where the link may be selectively disconnected or "unlatched" when it is desired to retract the sleeve and expose the hemostatic implant. Thus, the methods of the present invention will preferably further comprise unlatching the sleeve before retracting the sleeve. In a specific embodiment, the unlatching comprises distally advancing a key over the latch to effect the desired unlatching. As described above in connection with the apparatus of the present invention, an exemplary latch and key comprises a spring-like element which is secured over an exterior portion of the shaft. The spring-like element typically projects radially outward from the shaft when unconstrained. In this way, the spring-like latch element can engage the protective sleeve to prevent proximal retraction of the sleeve. The latch can be released by advancing a cylindrical or other key element distally over the shaft to depress the spring-like latch element.

In a further preferred aspect of the method of the present invention, a proximal portion of the sleeve will be configured to lie proximal to, i.e., outside of, the tissue tract when the occlusion element is deployed in the blood vessel lumen. Usually, the key element will lie further proximal of the sleeve, permitting the user to manually deploy the key to unlock the latch and to further manually retract the protective sleeve by manually clasping an exposed portion of the sleeve and pulling it proximally from the tissue tract. Typically, the sleeve will have a length in the range from 2 cm to 30 cm, more typically from 5 cm to 15 cm.

In a still further preferred aspect of the method, the hemostatic implant will be constrained to prevent it from being displaced proximally while the shaft is being introduced through the tissue tract. In particular, the backstop or other element may be fixed to the shaft in a location selected to engage the hemostatic implant or an extension thereof to prevent the implant from being displaced proximally, either as the shaft is being introduced or more likely as the protective sleeve is being proximally retracted over the implant. Usually, the backstop or other element will be slidably mounted over the shaft so that it may be held in place as the occlusion element is retracted past the hemostatic implant.

In a specific aspect of the method of the present invention, radiopaque markers on or within the shaft or hemostatic implant are used to verify the location of implant prior to release. Inclusion of radiopaque markers on the delivery shaft is particularly useful when no radiopaque material is incorporated within the hemostatic implant. Preferably, there will be at least two distinct radiopaque bands, with one at each end of the implant. By observing the orientation of the two markers, the physician can determine whether the implant is properly aligned adjacent to the vascular penetration or has inadvertently advanced into a lumen of the blood vessel prior to deployment. In particular, by measuring or visually assessing the apparent distance between the bands when the device is being fluoroscopically imaged from an anterior aspect, the apparent distance between the bands will be longer if the hemostatic implant is within the blood vessel lumen than if it is within the tissue tract immediately above the blood vessel wall penetration. Such apparent differences in the positions of the two radiopaque marker bands results from the foreshortening of the vertical angle at the entry through the wall penetration into the blood vessel lumen. For example, if the tissue tract is disposed at a 45.degree. angle with respect to the horizontal orientation of the blood vessel lumen, in an anterior view, the marker bands will appear to be approximately 30% closer to each other than they would in the horizontal view when they are present in the blood vessel lumen.

BRIEF DESCRIPTION OF THE DRAWINGS

FIG. 1 illustrates an exemplary sealing apparatus constructed in accordance with the principles of the present invention, shown in section.

FIG. 1A is a detailed view of a distal portion of the sealing apparatus of FIG. 1, shown in partial section.

FIGS. 3-7 illustrate the further steps of deployment of the hemostatic implant from the apparatus of FIGS. 1 and 2.

FIGS. 8A-8I illustrate placement and deployment of the hemostatic implant using the apparatus of FIGS. 1 and 2 through a vascular sheath placed in a blood vessel.

FIGS. 15A-15F illustrate an alternative hemostatic implant protocol.

DETAILED DESCRIPTION OF THE INVENTION

Figure 2:
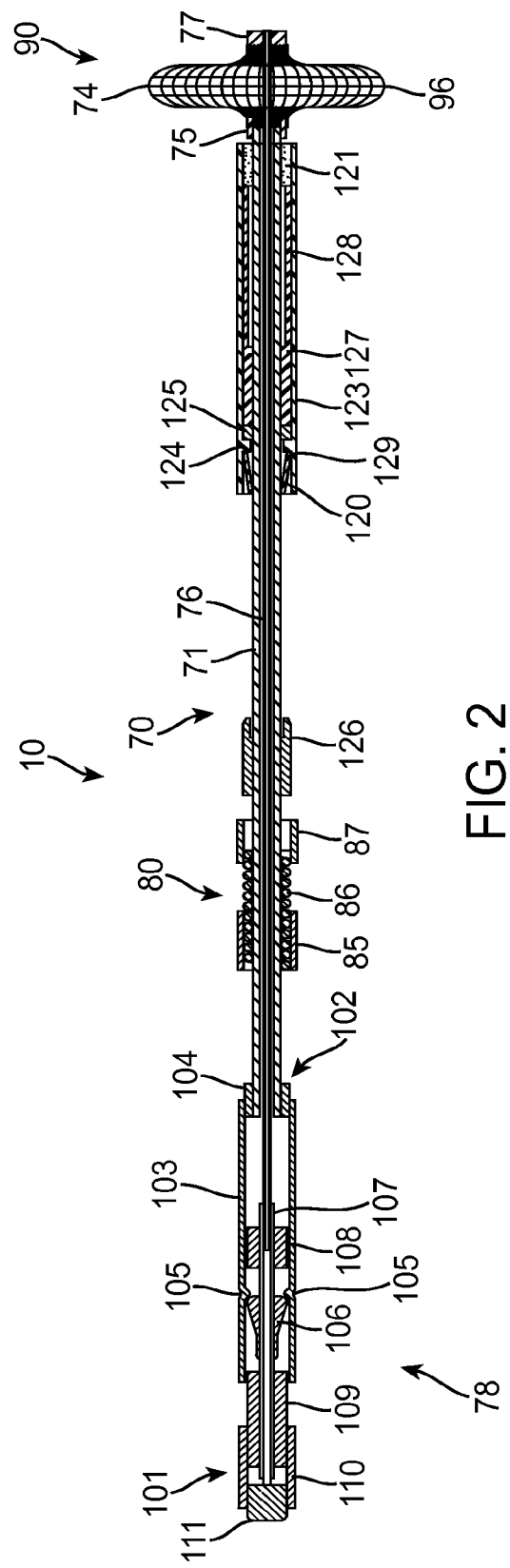
FIG. 2 is a cross-sectional view of the sealing apparatus of FIG. 1, shown with an expanded occlusion element.

Referring to FIGS. 1 and 1A, an exemplary sealing apparatus 10 constructed in accordance with the principles of the present invention comprises a shaft assembly 70 including an outer tube 71 and an inner rod 76. An expansible occlusion element 90 is mounted at a distal end (to the right in FIGS. 1 and 1A) of the shaft assembly 70 and includes a radially expansible mesh 74 covered by an elastomeric membrane 96. A handle assembly 78 is attached to a proximal end of the shaft assembly 70 and is operatively attached to both the outer tube 71 and inner rod 76 so that the inner rod can be axially advanced and retracted relative to the outer tube. The inner rod 76 and outer tube 71 are coupled together at the distal tip of the sealing apparatus 10 by a plug 77 and a proximal anchor 75, respectively. The occlusion element 90 is held between the plug 77 and the proximal anchor 75 so that axial retraction of the rod in the proximal direction (to the left as shown in FIGS. 1 and 1A) foreshortens the occlusion element 90, causing the occlusion element to expand radially, as shown for example in FIG. 2.

Axial advancement and retraction of the rod 76 relative to the outer tube 71 is effected using the handle assembly 78. The handle assembly 78 includes a cylindrical body 103 attached to the proximal end of the outer tube 71 by a bushing 104 so that the body 103 will remain fixed relative to the outer tube as the inner rod 76 is retracted and advanced. The inner rod is retracted and advanced by a slide assembly 101 which includes a short tube 110 fixedly attached to an endcap 111 and a slide cylinder 109. The inner rod 76 is secured by tube element 107 which carries locking element 106 and bearing elements 108 and 109. Bearing element 109 is attached to proximal grip 101 and the assembly of the grip 101 and tube element 107 can slide freely within the interior of the cylindrical body 103 so that the rod 76 may be proximally retracted relative to the body 103 and outer tube 71, as shown in FIG. 2. Once the expansible occlusion element 90 has been radially expanded, the rod 76 will remain retracted and is held in place by locking element 106 which is pulled over a detent 105, again as shown in FIG. 2. An alignment bushing 108 is provided in the interior of the cylindrical body 103 to maintain alignment of the slide assembly 101 relative to the cylindrical body.

The sealing apparatus of the present invention may optionally include a tensioning mechanism 80 which includes a coil spring 86, a gripping element 85, and a coupling element 87. The tensioning mechanism 80 may be selectively positioned along the length of shaft assembly 70, and will provide a tension determined by the constant of coil spring 86 to hold the expanded occlusion element 74 against the vascular penetration, as described in more detail in copending, commonly-owned application Ser. No. 10/974,008, the full disclosure of which is incorporated herein by reference. As described thus far, the construction and use of the sealing apparatus including shaft assembly 70, handle assembly 78, tensioning mechanism 80, and expansible occlusion element 90 are generally the same as illustrated in copending application Ser. No. 10/974,008. The present invention is directed at modifications and improvements to the earlier device for delivering a hemostatic implant into the tissue tract generally above the vascular wall penetration, as will be described in more detail below.

As best seen in FIG. 1A, hemostatic implant 121, which will typically be a biodegradable polymer as described in more detail above, is carried coaxially or in parallel over the outer tube 71 near the distal end thereof proximal to the expansible occlusion element 90. While the hemostatic implant 121 is shown to be positioned coaxially over outer tube 71 in FIG. 1A, it will often be desirable to modify or reposition the implant in order to facilitate release from the sealing apparatus after the implant has been deployed. More simply, the hemostatic implant could be axially split to allow it to partially open after it is hydrated and facilitate passage of the collapsed occlusion element 74 as the sealing apparatus is being withdrawn. Alternatively, the hemostatic implant may be reconfigured and carried laterally (i.e., to one side of) with respect to the shaft of the sealing apparatus, as described in more detail hereinafter with respect to FIGS. 9A and 9C. The hemostatic implant 121 could alternatively be carried on the inner surface of a protective sleeve 123 which is slidably carried over the outer tube 71. The protective sleeve 123 slides over a backstop 127 which is slidably mounted over the outer tube 71 and which is prevented from moving proximally by stop member 125 which is fixed to the outer surface of the outer tube. Backstop 127 has a distal end 128 which engages a proximal end of the hemostatic implant 121. Thus, by proximally retracting the protective sleeve 123, the hemostatic implant 121 can be exposed to the tissue tract and released from the sealing apparatus.

Accidental axial retraction of the protective sleeve 123 is prevented by a latch mechanism including a latch element 120 and a key 126 (FIGS. 1 and 2). The latch element 120 is typically a spring-loaded component, for example a conical spring having a narrow diameter end attached to the outer tube 71 and a flared or larger diameter end 129 which engages a stop ring 124 formed on the inner surface of the protective sleeve 123. So long as the flared end 129 of the latch element 120 remains in its flared or open configuration, as illustrated in FIG. 1A, accidental proximal retraction of the sleeve is prevented. It is further noted that the stop ring 124 engages stop member 125 of the backstop 127 preventing accidental distal movement of the protective sleeve 123. Thus, when the sealing apparatus 10 is introduced to a tissue tract, as described in more detail below, movement of the protective sleeve 123 in either the distal or proximal direction is inhibited.

To allow selective proximal retraction of the protective sleeve 123, the key 126 (FIGS. 1 and 2) may be axially advanced to engage the latching element 120, as illustrated in FIG. 3. The key 126 fits inside of the protective sleeve 123 and depresses or radially contracts the latch element 120 so that it fits within the interior circumference of the stop ring 124, thus allowing proximal retraction of the protective sleeve 123, as shown in FIG. 4.

Once the key 126 has engaged and constrained the latch element 120, as shown in FIG. 3, the protective sleeve 123 may be proximally withdrawn past the hemostatic implant 121 and the backstop 127, as shown in FIG. 4. Thus, the hemostatic implant 121 will be released from constraint and exposed to the environment in the tissue tract. The environment in the tissue tract will include blood and other body fluids which can hydrate the hemostatic implant 121, causing swelling as shown in FIG. 4. The swelling will continue, as shown in FIG. 5, and the radially expanded occlusion element 90 can be collapsed using the handle assembly, as shown in FIG. 5. The collapsed occlusion element 90 can then be proximally withdrawn into distal receptacle 128 of the backstop assembly 127, as shown in FIG. 6 (where an annular space may be provided to accommodate the occlusion element). When the occlusion element has been fully withdrawn within the backstop 127, the hemostatic implant is completely released, as shown in FIG. 6, and the remaining portions of the sealing apparatus can be pulled away from the hemostatic implant, as shown in FIG. 7.

Figure 8B:
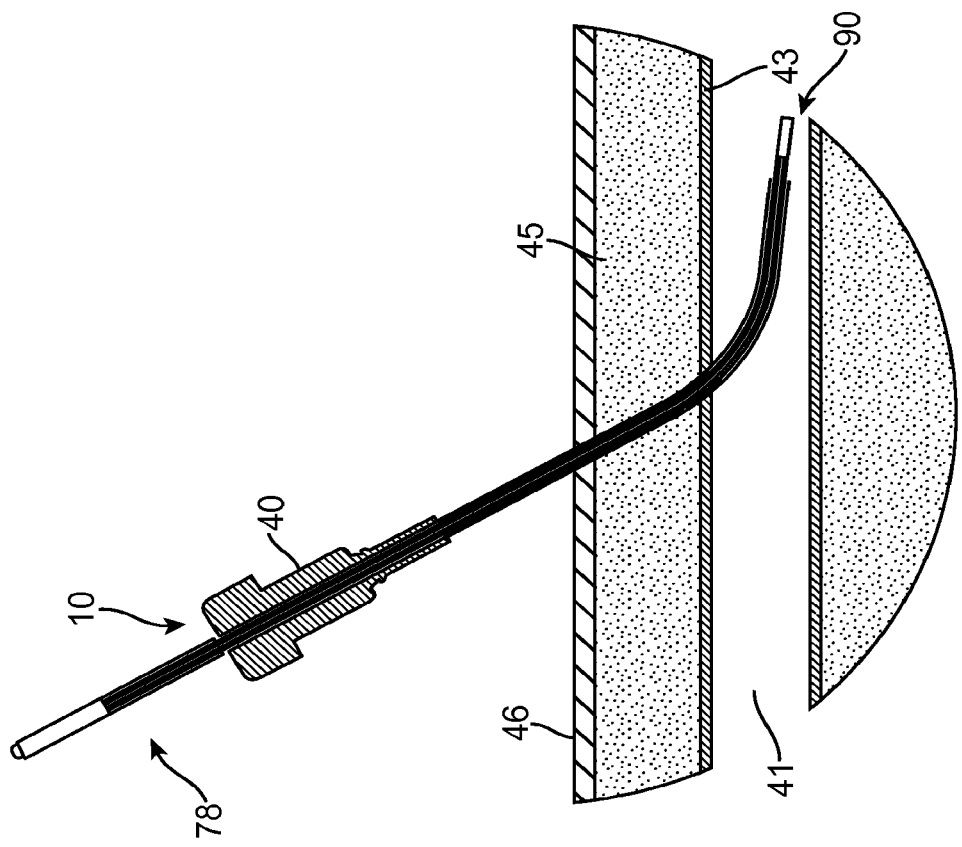
Figure 8A:
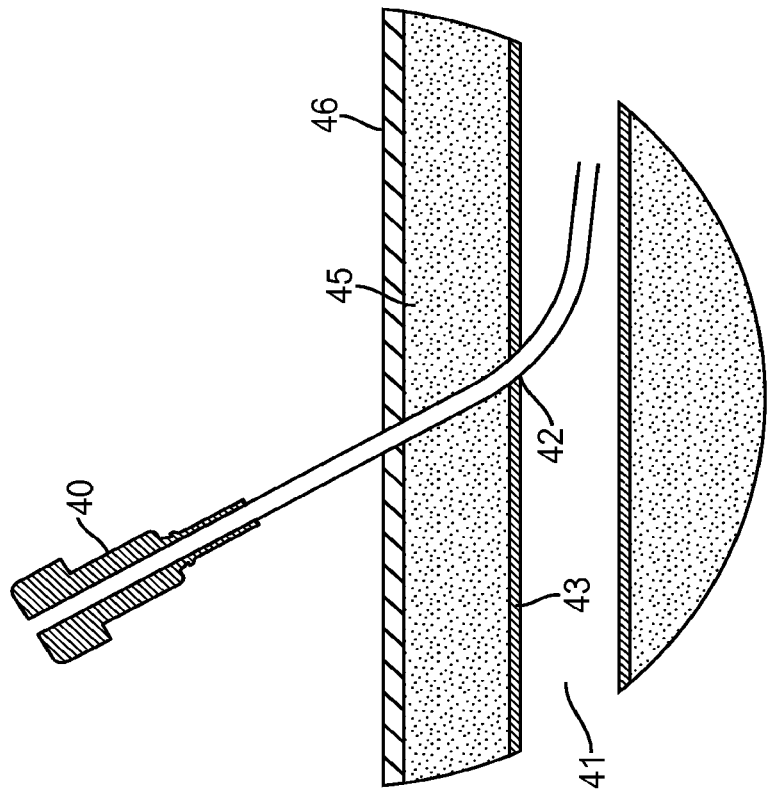

Referring now to FIGS. 8A-8I, deployment and use of the sealing apparatus 10 of the present invention through an introducer sheath 40 will be described in more detail. Introducer sheath 40 will typically be in place within a blood vessel lumen 41 passing from the skin surface 46 through tissue 45 in a tissue tract. A vascular wall penetration 42 will thus be present in the vascular wall 43, all as shown in FIG. 8A. The sealing apparatus 10 is then introduced through the access sheath 40 so that the expansible occlusion element 90 passes out through the distal end of the sheath, as shown in FIG. 8B. Handle assembly 78 will remain outside of the sheath and accessible to the user so that the slide assembly 101 may be pulled relative to the cylindrical body 103 to radially expand the occlusion element 90, as shown in FIG. 8C. The vascular access sheath 40 may then be withdrawn over the exterior of the sealing apparatus 10 while the sealing apparatus is simultaneously withdrawn to seat the expanded occlusion element 90 against the vascular penetration 42, as shown in FIG. 8D.

Figure 8F:
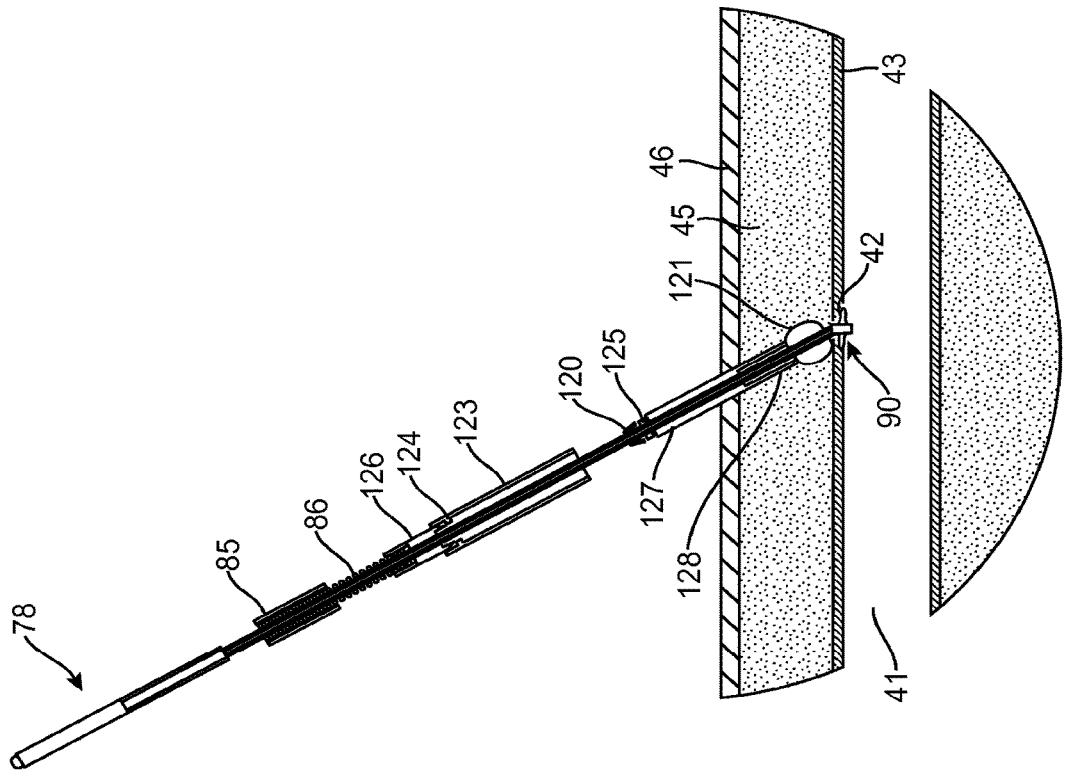
Figure 8E:
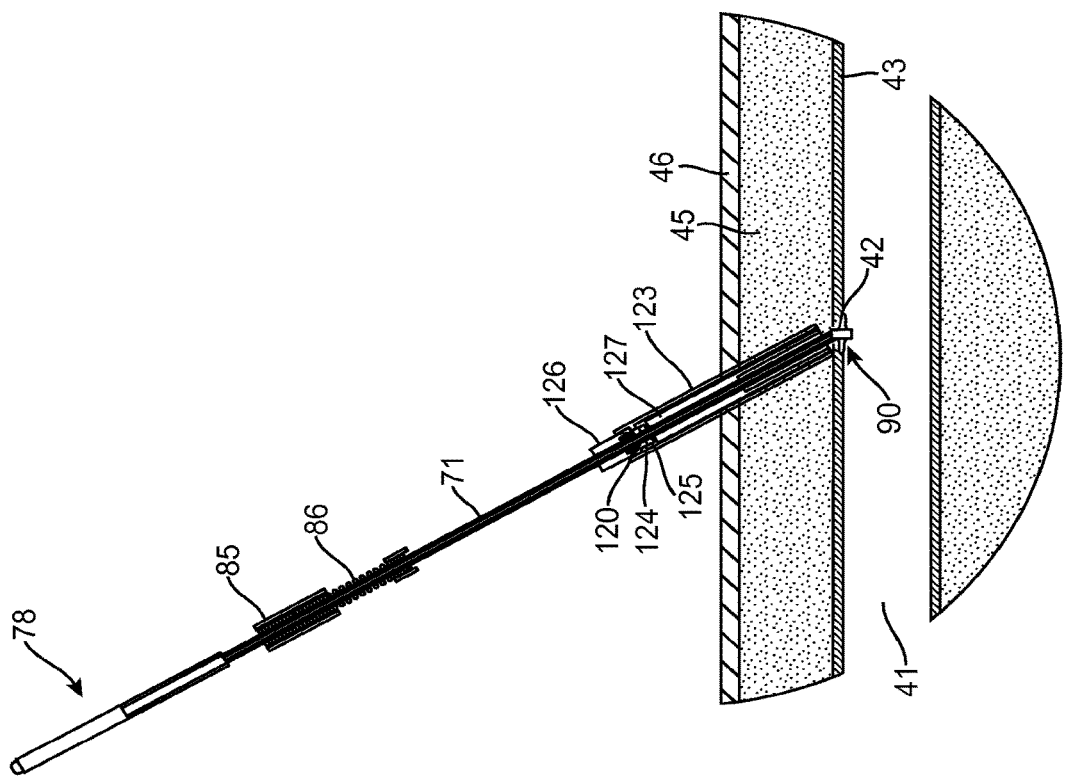
Figure 8I:
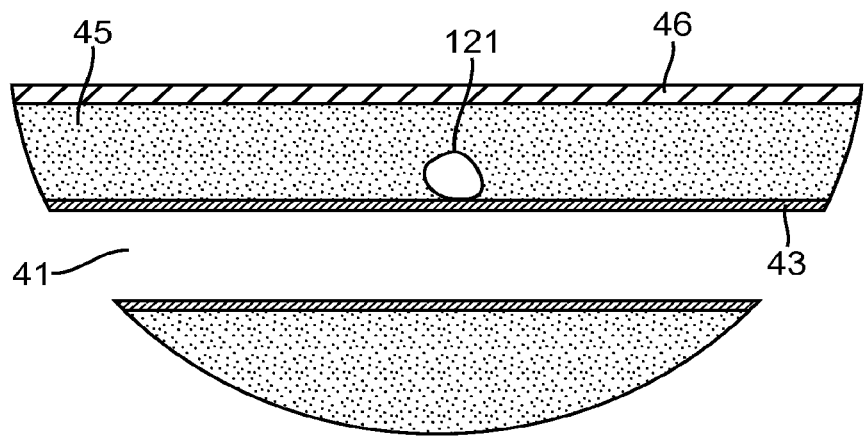

At that point, the protective sleeve 123 and key 126 become exposed and available to the user for manipulation. The key may then be distally advanced over the outer tube 71 so that the key engages and depresses the latch 120 (FIG. 1A) as illustrated in FIG. 8E. The key 126 and protective sleeve 123 may then be manually pulled in a proximal direction over the outer tube 71 to release the hemostatic implant 121, as shown in FIG. 8F. The expandable element 90 may then be collapsed, as shown in FIG. 8G, and the collapsed element withdrawn into the receptacle 128 of the backstop 127 of the sealing apparatus, as shown in FIG. 8H. The entire sealing apparatus 10, except for the hemostatic implant 121, may then be withdrawn from the tissue tract, leaving the hemostatic implant 121 in place over the now closed vascular wall penetration, as shown in FIG. 8I. The hemostatic implant, which may optionally carry the antiproliferative, coagulation promoting, and/or radiopaque substances described above, will remain in place inhibiting bleeding and allowing the vascular wall penetration to heal. Over time, the hemostatic implant 121 will preferably biodegrade, leaving a healed tissue tract and vascular wall penetration which are usually suitable for re-entry at a subsequent time.

Figure 9A:
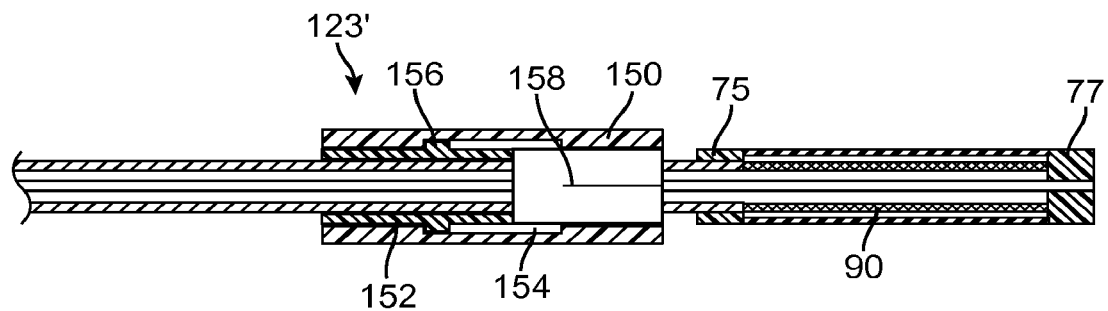
FIGS. 9A-9C illustrate a sealing apparatus in accordance with the present invention having a protective sleeve including an outer sleeve and an inner release sheath.
Figure 9B:
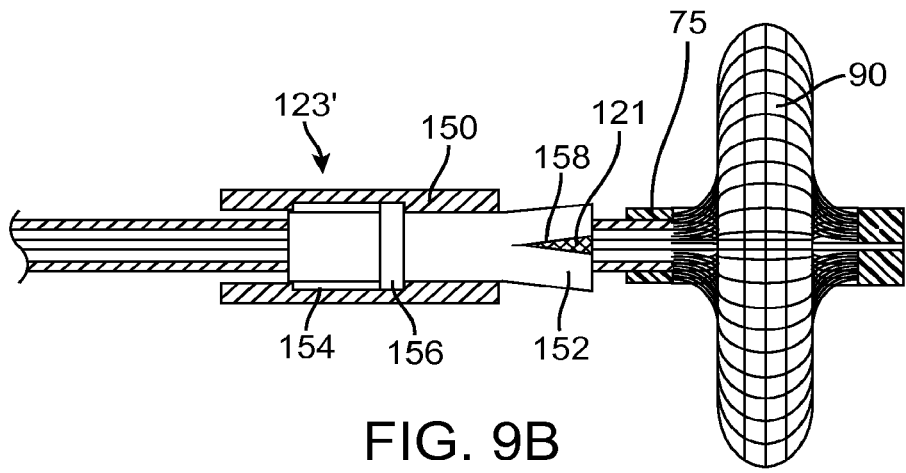
Figure 9C:
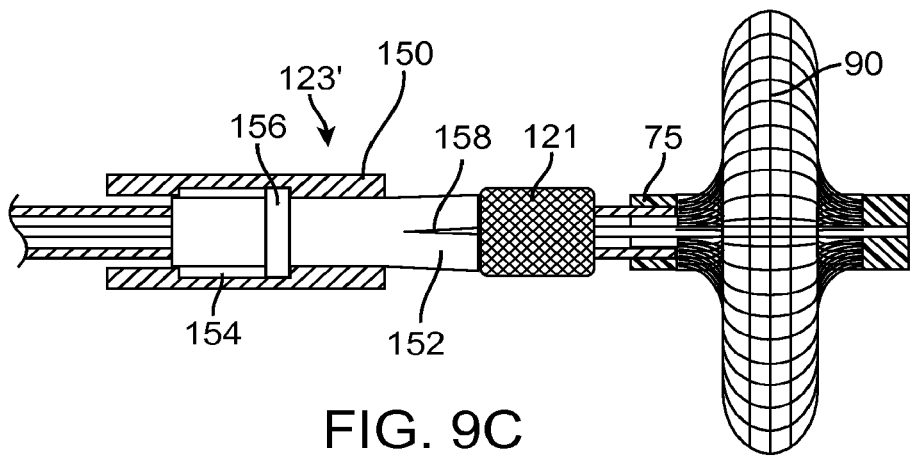

Referring now to FIGS. 9A-9C, a protective sleeve 123' comprises an outer sleeve 150 and an inner release sheath 152. The outer sleeve 150 and inner release sheath 152 are separately retractable so that the outer sleeve may first be retracted relative to the hemostatic implant 121 (FIG. 9B) while the inner release sheath initially remains over the implant. The release sheath 152 will thus provide an anti-friction interface so that the outer sleeve 150 slides over the implant 121 with reduced sticking The inner release sheath 152 is preferably formed from a relatively lubricious or slippery material and will preferably include an axial opening or slit 158 which permits the distal portion thereof to partially open after the outer sleeve 150 has been retracted, as shown in FIG. 9B. Once the outer sleeve 150 has been retracted to relieve constraint over the hemostatic implant, the inner sleeve may then be retracted to completely release the hemostatic implant, as shown in FIG. 9C. Conveniently, the outer sleeve 150 may be coupled to the inner release sheath 152 so that proximal retraction of the outer sleeve will automatically retract the inner release sheath at the proper point in travel. For example, a cavity or channel 154 may be formed in an inner surface of the outer sleeve 150 and a ring or other engaging element 156 may be formed on the outer surface of the inner release sheath 152. Initially, the ring 156 will be positioned at the proximal end of the cavity or channel 154, as shown in FIG. 9A. After the outer sleeve 150 has been retracted so that it no longer lies over the implant 121, the ring may then engage a distal end of the cavity or channel 154, as shown in FIG. 9B, and engage the ring 156, allowing the outer sleeve to then pull the inner sleeve proximally, as shown in FIG. 9C, to fully release the hemostatic implant 121.

Figure 10A:
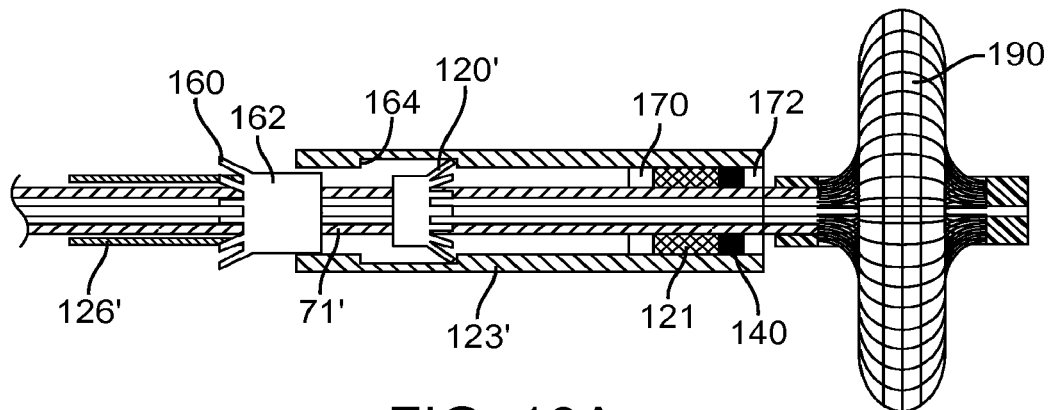
FIGS. 10A-10C illustrate a sealing apparatus in accordance with the present invention having a key latch mechanism which engages the protective sleeve and may be used to proximally withdraw the sleeve to deploy the hemostatic implant.
Figure 10B:
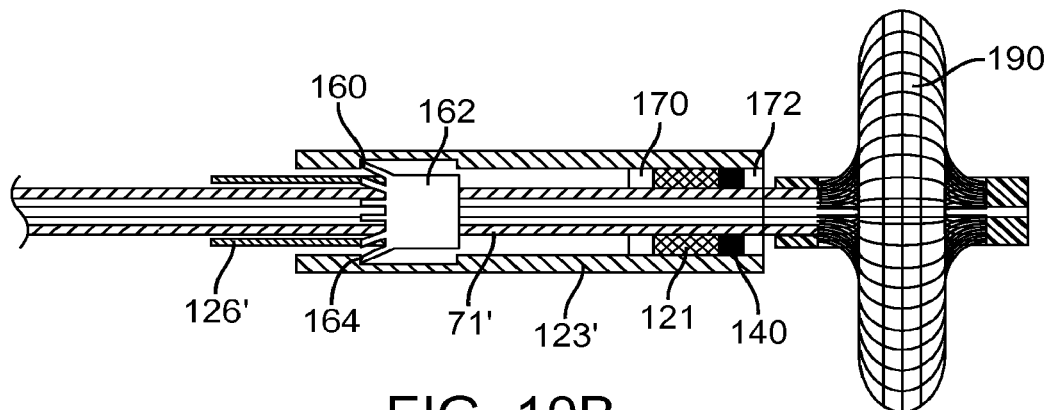
Figure 10C:
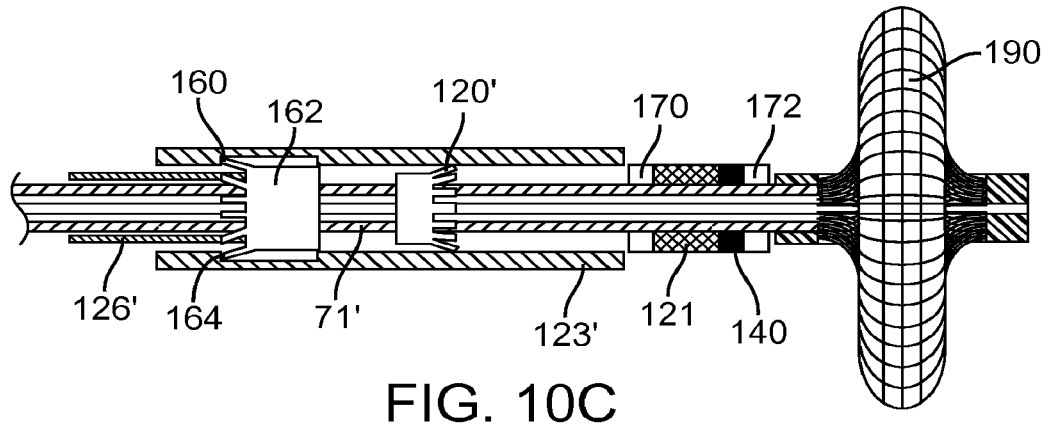

Referring now to FIGS. 10A-10C, it is also possible to selectively couple the key 126' to a protective sleeve 123'. The key 126' has a coupling element, such as plurality of proximally disposed barbs 160 at its distal end. The key 126' may be advanced into the protective sleeve 123' where a distal end 162 of the key 126' engages latching element 120' on the outer tube 71'. Latching mechanism 120' may conveniently comprise a plurality of barbs so that advancement of the key 123' radially closes the barbs allowing the protective sleeve 123' to be proximally retracted relative to the tube 71'. Once the key 126' is fully distally advanced, as shown in FIG. 10B, the proximally disposed barbs 160 will engage an inner lip 164 at the proximal end of the protective sleeve 123'. Thus, as the key 126' is proximally retracted, as shown in FIG. 10C, the key will pull the protective sleeve 123' in a proximal direction, thus exposing the implant 121.

A further aspect of the present invention is illustrated in FIGS. 10A and 10B. Radiopaque marker bands 170 and 172 may be provided at the proximal and distal ends of the implant 121, respectively. Usually, these bands will be disposed on the outer tube 71', but they could also be disposed on or incorporated within the hemostatic implant 121. In either case, they are useful to evaluate positioning of the hemostatic implant prior to deployment, as described in more detail below in FIGS. 13A, 13B, 14A, and 14B.

Figure 11A:
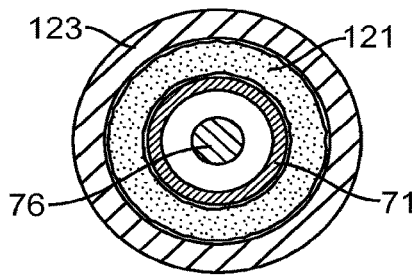
FIGS. 11A and 11B illustrate a hemostatic implant which is coaxially disposed about the shaft of the deployment apparatus of the present invention.
Figure 11B:
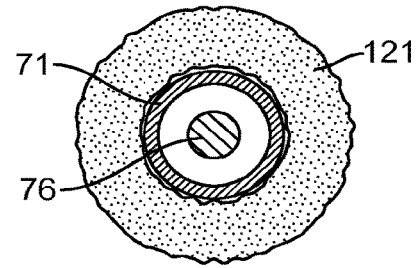

Referring now to FIGS. 11A and 11B, the hemostatic implant 121 may be disposed coaxially over the outer tube 71 and in a rod 76. By proximally retracting the protective sleeve 123, the implant 121 is released and can hydrate as shown in FIG. 11B. As described previously, however, it will still be necessary to withdraw the outer tube 71 as well as the collapsed occlusion element 90 past the hemostatic implant 121. When the hemostatic implant 121 fully circumscribes the outer tube 71, however, both the tube 71 and the collapsed occlusion element 90 can tend to dislodge the implant within the tissue tract.

Figure 12A:
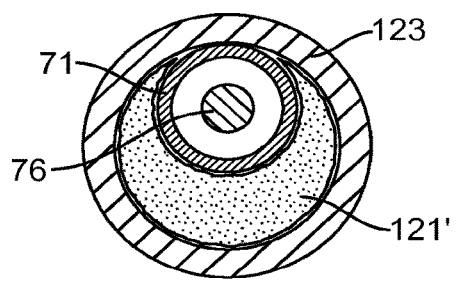
FIGS. 12A and 12B illustrate the hemostatic implant which is laterally disposed relative to the shaft of the deployment mechanism.
Figure 12B:
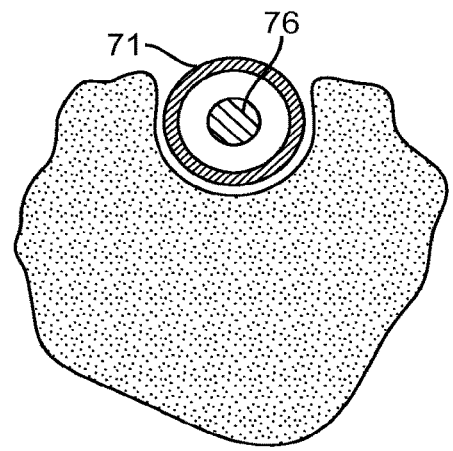

Therefore, in some instances, it will be desirable to modify the geometry of the implant to facilitate withdrawal of the outer tube and the collapsed occlusion element. For example, as shown in FIGS. 12A and 12B, hemostatic implant 121' can be formed with a crescent-shaped cross-section so that it does not fully circumscribe the outer tube 71 which carries it. By laterally displacing the outer tube 71 and inner rod 76 within the protective sleeve 123, as shown in FIG. 12A, the volume of the hemostatic implant 121 will be generally the same as that shown in FIG. 11A. When the protective sleeve 123 is withdrawn, however, as shown in FIG. 12B, the hemostatic implant 121 will hydrate and expand laterally on one side of the outer tube 71, as shown in FIG. 12B. By disposing the outer tube 71 and collapsed occlusive element 90 to one side of the implant, it is much easier to withdraw the apparatus and collapsed occlusion member past the implant without dislodging the implant within the tissue track.

Figure 13A:
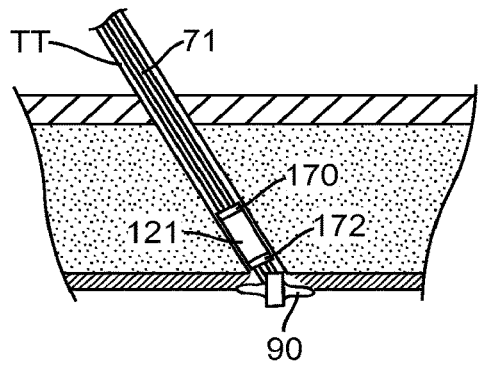
FIGS. 13A and 13B illustrate how aligned radiopaque markers may be utilized to determine that the hemostatic implant is properly located prior to deployment.
Figure 13B:
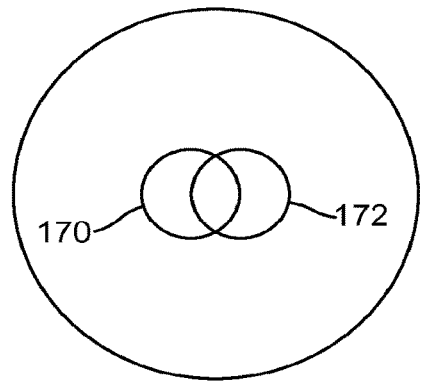
Figure 14A:
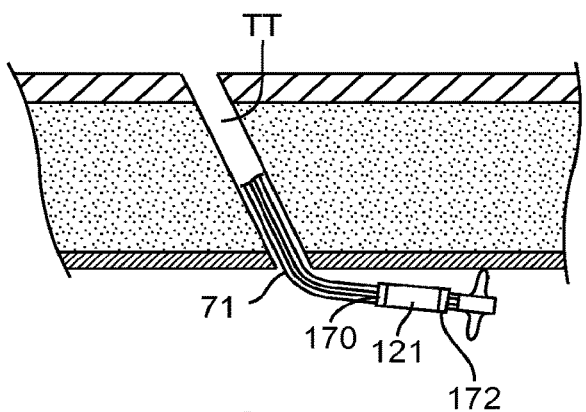
FIGS. 14A and 14B illustrate how such radiopaque markers would appear when the hemostatic implant is improperly positioned prior to deployment.
Figure 14B:
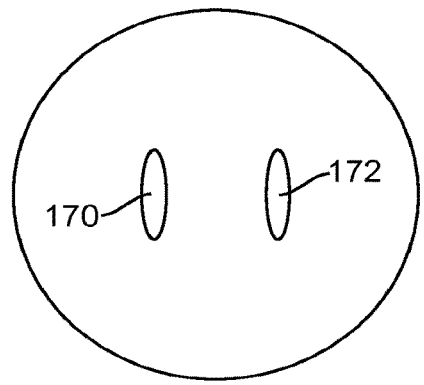

Referring now to FIGS. 13A and 13B, the radiopaque markers 170 and 172 can be used to determine whether the hemostatic implant 121 is oriented properly prior to deployment. For simplicity, the protective sleeve and other components of the deployment system are not shown in FIGS. 13A and 13B (or in 14A and 14B as described below). The radiopaque markers 170 and 172 may be formed as part of the deployment instrument, for example being placed on outer tube 71, and/or may be formed as part of the hemostatic implant 121. In either case, when the deployment apparatus is properly oriented as shown in FIG. 13A, the radiopaque markers 170 and 172 will appear to be stacked generally vertically when viewed in an anterior view, as shown in FIG. 13B. In contrast, if the apparatus has been improperly deployed so that the hemostatic implant has been advanced into the vessel lumen past the tissue tract TT as shown in FIG. 14A, then the radiopaque markers 170 and 172 will be spaced apart in the anterior view as shown in FIG. 14B. As these views will be readily distinguishable by the physician using conventional fluoroscopy, the radiopaque markers provide a convenient and reliable indicator of when it is acceptable to deploy the hemostatic implant.

Referring now to FIGS. 15A through 15F, a method for hemostasis of a puncture site in a body lumen employing the device 270 of FIG. 1 is illustrated. FIG. 15A depicts an existing introducer sheath 240 advanced through an opening in a skin surface 246, tissue tract in fascia 245 and vessel wall 243 and seated in a vessel lumen 241 at the completion of a catheterization procedure. Device 270 is then inserted through the hub of the sheath 240 and is advanced until the expansible member 274 is outside the sheath 240 and in the vessel lumen 241, as shown in FIG. 15B. This positioning may be indicated by a mark or feature on the catheter 271 or the handle assembly 278.

As shown in FIG. 15C, the expansible member 274 is then deployed by operation of the handle assembly 278. The sheath 240 is then slowly pulled out of the body, placing the expansible member 274 against the inner wall of the vessel 243 at the puncture site 242. As the sheath 240 is removed, the grip member 285 which is slidably disposed over the catheter shaft 271 and the handle assembly 278 are revealed.

Sheath 240 is then discarded, leaving deployed expansible member 274 seated at the puncture site 242 and the bio-chemical chamber/region 351 in the tissue tract 247 as shown in FIG. 15D. If the device is equipped with the safety seal 355 as in device 270, then the safety seal 355 is removed by pulling the tab 356 proximally along the catheter shaft.

Referring now to FIG. 15E, once safety seal 355 is removed, the grip element 285 is grabbed and pulled in a proximal direction. Grip 285 is moved proximally to provide adequate amount of tension to the deployed expansible member 274 to achieve hemostasis. Typically, the amount of tension applied to the expansible member 274 is in the range of 0.5 ounces to 30 ounces. In particular, proximal movement of grip 285 causes simultaneous elongation of the tensioning coil 286, causing the expansible member to locate and temporarily close the puncture site 242, and displacement of the bio-chemical seal 353, exposing the bio-chemical agent 352 to the surrounding tissue at a predetermined distance from the puncture site. The elongated position of coil 86 is maintained by application of a small external clip 250 to the catheter and seated against the surface of the skin 246, as shown in FIG. 15E. Device 270 is left in this position for a period of time to allow the bio-chemical agent 352 to reconstitute with the fluids in the tissue tract 247, generating coagulum. Clip 250 is then removed and the expansible member 274 is collapsed by manipulation of the handle assembly 278. Device 270 is then removed, leaving the active bio-chemical agents 352 and the coagulum in the tract 247 and adjacent the vessel puncture site 242, as shown in FIG. 15F. Additional finger pressure at the puncture site may be required to allow the coagulum to seal the small hole left in the vessel wall after removal of the device.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for sealing a blood vessel penetration disposed at the end of a tissue tract, comprising:

providing an apparatus including a shaft having an axis, an occlusion element, and a hemostatic implant disposed over and in contact with an exterior surface of at a distal end of the shaft, the hemostatic implant having a first mass on a first lateral side of the shaft and a second mass on a second lateral side opposite the first lateral side, the first mass being greater than the second mass such that the hemostatic implant is asymmetrically mounted relative to the axis on the exterior surface of the shaft;

introducing the shaft through the tissue tract to concurrently position both the occlusion element and the hemostatic implant in a lumen of the blood vessel, wherein the hemostatic implant is maintained in a position between a protective sleeve and the exterior surface of the shaft while the shaft is being introduced;

deploying the occlusion element;

retracting the apparatus to seat the deployed occlusion element against the blood vessel penetration to inhibit blood flow from the blood vessel into the tissue tract and to position the hemostatic implant within the tissue tract;

retracting the protective sleeve to expose the hemostatic implant, wherein the first mass of the hemostatic implant is greater than the second mass of the hemostatic implant such that the hemostatic implant hydrates and expands laterally to release from the first lateral side of the shaft, thereby facilitating withdrawal of the shaft and occlusion element past the expanded hemostatic implant;

collapsing the occlusion element; and withdrawing the shaft and collapsed occlusion element past the hemostatic implant which remains in the tissue tract to completely biodegrade therein over a period of time to leave no material behind, wherein the shaft and the hemostatic implant have been advanced through the tissue tract prior to deploying the occlusion element.

2. A method as in claim 1, wherein the protective sleeve is latched to the shaft while the shaft is introduced, further comprising unlatching the sleeve before retracting the sleeve.

3. A method as in claim 2, wherein unlatching comprises distally advancing a key over a latch on the shaft.

4. A method as in claim 3, wherein the key and a proximal end of the sleeve lie proximally of the tissue tract when the occlusion element is deployed in the blood vessel lumen, wherein unlatching the latch and retracting the sleeve are performed by direct manipulation with a user's hands.

5. A method as in claim 4, wherein the hemostatic implant is prevented from being displaced proximally by a back stop on the shaft while the sleeve is retracted and while the shaft is withdrawn.

6. A method as in claim 4, wherein the key couples to the protective sleeve and the sleeve is retracted by retracting the key.

7. A method as in claim 1, wherein the protective sleeve comprises an outer sleeve and an inner release sheath, wherein the outer sleeve is retracted first while the inner release sheath inhibits sticking between the outer sleeve and the hemostatic implant.

8. A method as in claim 7, wherein the inner release sheath is split so that the inner release sheath opens over the hemostatic implant as the outer sleeve is retracted.

9. A method as in claim 1, wherein the hemostatic implant comprises a swellable, biodegradable polymer, wherein the polymer is not fully hydrated when covered by the protective sleeve and hydrates when exposed by retracting the protective sleeve.

10. A method as in claim 9, wherein the biodegradable polymer comprises a material selected from the group consisting of polyethylene glycols, collagens, and gelatins.

11. A method as in claim 1, wherein the hemostatic implant comprises an active agent comprising an anti-proliferative agent selected from the group consisting of sirolimus and paclitaxel, wherein the active agents are incorporated in a degradable carrier comprising a material selected from the group consisting of polylactic acid and poly(lactide-co-glycolide).

12. A method as in claim 1, wherein the hemostatic implant comprises an active agent which comprises an anti-proliferative agent selected from the group consisting of sirolimus and paclitaxel, or a coagulant selected from the group consisting of thrombin and tissue factor.

13. A method as in claim 12, wherein the active agent is incorporated in a nanoparticle.

14. A method as in claim 13, wherein the nanoparticles have an average size in the range from 10 nm to 100 µm.

15. A method as in claim 1, wherein at least a portion of the hemostatic implant or shaft is radiopaque, wherein the method further comprises observing the hemostatic implant to determine that the hemostatic implant has a correct orientation before the protective sleeve is retracted.

16. A method as in claim 1, wherein the shaft is advanced through an introducer sheath which is present in the tissue tract.

17. A method as in claim 16, further comprising removing the introducer sheath over the apparatus after the shaft has been introduced therethrough.

18. A method as in claim 16, wherein the shaft is introduced without a guidewire.

19. A method as in claim 1, wherein the hemostatic implant comprises a wrapped sheet at least partially circumscribing the shaft.

* * * * *